US008655259B2

(12) United States Patent  
Brown et al.

(10) Patent No.: US 8,655,259 B2  
(45) Date of Patent: *Feb. 18, 2014

(54) SYSTEM AND METHOD FOR MONITORING A PHYSIOLOGICAL CONDITION

(75) Inventors: Stephen J Brown, Woodside, CA (US); Roger J. Quy, San Mateo, CA (US)

(73) Assignee: Robert Bosch Healthcare Systems, Inc., Palo Alto, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 10/673,045

(22) Filed: Sep. 26, 2003

(65) Prior Publication Data

US 2004/0219500 A1 Nov. 4, 2004

Related U.S. Application Data

(63) Continuation of application No. 09/971,785, filed on Oct. 4, 2001, now abandoned, which is a continuation of application No. 09/119,546, filed on Jul. 20, 1998, now Pat. No. 6,330,426, which is a continuation-in-part of application No. 08/953,883, filed on Oct. 20, 1997, now abandoned, which is a continuation-in-part of application No. 08/757,129, filed on Dec. 3, 1996, now Pat. No. 6,144,837, which is a continuation-in-part of application No. 08/334,643, filed on Nov. 4, 1994, now Pat. No. 5,601,435, and a continuation of application No. 08/958,786, filed on Oct. 29, 1997, now Pat. No. 5,913,310, which is a continuation-in-part of application No. 08/857,187, filed on May 15, 1997, now Pat. No. 5,918,603, which is a continuation of application No. 08/247,716, filed on May 23, 1994, now Pat. No. 5,678,571.

(51) Int. Cl.  
*G09B 5/00* (2006.01)

(52) U.S. Cl.  
USPC ............................................ 434/350; 434/322

(58) Field of Classification Search  
USPC ........... 434/118, 247, 318, 265, 30, 7 R, 308, 434/262, 362, 365, 236, 350, 322; 600/301, 600/322, 316; 725/10; 463/1; 702/19  
See application file for complete search history.

(56) References Cited

U.S. PATENT DOCUMENTS

| | | | |
|---|---|---|---|
| 3,426,150 | A | 2/1969 | Tygart |
| 3,566,365 | A | 2/1971 | Rawson et al. |
| 3,566,370 | A | 2/1971 | Worthington, Jr. et al. |
| 3,581,072 | A | 5/1971 | Nymeyer |
| 3,768,014 | A | 10/1973 | Smith |
| 3,808,502 | A | 4/1974 | Babilius |
| 3,811,116 | A | 5/1974 | Takeuchi et al. |
| 3,883,235 | A | 5/1975 | Lynn et al. |
| 3,910,257 | A * | 10/1975 | Fletcher et al. ............... 600/483 |
| 3,920,005 | A | 11/1975 | Gombrich et al. |
| 3,996,928 | A | 12/1976 | Marx |
| 4,004,577 | A | 1/1977 | Sarnoff |
| 4,051,522 | A | 9/1977 | Healy et al. |
| 4,060,915 | A | 12/1977 | Conway |
| 4,110,918 | A * | 9/1978 | James et al. ................... 434/262 |
| 4,130,881 | A | 12/1978 | Haessler et al. |
| 4,150,284 | A | 4/1979 | Trenkler et al. |
| 4,151,407 | A | 4/1979 | McBride et al. |
| 4,151,831 | A | 5/1979 | Lester |
| 4,173,971 | A | 11/1979 | Karz |
| 4,216,462 | A | 8/1980 | McGrath et al. |
| 4,227,526 | A | 10/1980 | Goss |
| 4,253,521 | A | 3/1981 | Savage |
| 4,259,548 | A | 3/1981 | Fahey et al. |
| 4,270,547 | A | 6/1981 | Steffen et al. |
| 4,282,604 | A * | 8/1981 | Jefferson ....................... 398/115 |
| 4,296,756 | A | 10/1981 | Dunning et al. |
| 4,347,568 | A | 8/1982 | Giguere et al. |
| 4,347,851 | A | 9/1982 | Jundanian |
| 4,360,345 | A | 11/1982 | Hon |
| 4,412,287 | A | 10/1983 | Braddock, III |
| 4,417,306 | A | 11/1983 | Citron et al. |
| 4,422,081 | A | 12/1983 | Woods et al. |
| 4,449,536 | A | 5/1984 | Weaver |
| 4,465,077 | A | 8/1984 | Schneider |
| 4,473,884 | A | 9/1984 | Behl |
| 4,518,361 | A | 5/1985 | Conway |
| 4,519,398 | A | 5/1985 | Lisiecki et al. |
| 4,531,527 | A | 7/1985 | Reinhold, Jr. |

| | | | | | | |
|---|---|---|---|---|---|---|
| 4,546,436 A | 10/1985 | Schneider et al. | | 5,120,421 A | 6/1992 | Glass et al. |
| 4,566,461 A | 1/1986 | Lubell et al. | | 5,128,552 A | 7/1992 | Fang et al. |
| 4,576,578 A | 3/1986 | Parker et al. | | 5,128,752 A | 7/1992 | Von Kohorn |
| 4,592,546 A | 6/1986 | Fascenda et al. | | 5,134,391 A | 7/1992 | Okada |
| 4,627,445 A | 12/1986 | Garcia | | 5,142,358 A | 8/1992 | Jason |
| 4,674,652 A | 6/1987 | Aten et al. | | 5,142,484 A | 8/1992 | Kaufman et al. |
| 4,686,624 A | 8/1987 | Blum et al. | | 5,143,378 A | 9/1992 | Joel |
| 4,694,490 A | 9/1987 | Harvey et al. | | 5,171,977 A | 12/1992 | Morrison |
| 4,695,954 A | 9/1987 | Rose et al. | | 5,176,502 A | 1/1993 | Sanderson et al. |
| 4,700,055 A * | 10/1987 | Kashkashian, Jr. ............ 235/379 | | 5,182,707 A | 1/1993 | Cooper et al. |
| 4,712,562 A | 12/1987 | Ohayon et al. | | 5,204,670 A | 4/1993 | Stinton |
| 4,722,349 A | 2/1988 | Baumberg | | 5,219,322 A | 6/1993 | Weathers |
| 4,729,381 A | 3/1988 | Harada et al. | | 5,222,020 A | 6/1993 | Takeda |
| 4,730,253 A | 3/1988 | Gordon | | 5,226,431 A | 7/1993 | Bible et al. |
| 4,731,726 A | 3/1988 | Allen, III | | 5,226,895 A | 7/1993 | Harris |
| 4,738,451 A | 4/1988 | Logg | | 5,227,874 A | 7/1993 | Von Kohorn |
| 4,749,354 A | 6/1988 | Kerman | | 5,228,450 A | 7/1993 | Sellers |
| 4,768,229 A | 8/1988 | Benjamin et al. | | 5,230,629 A | 7/1993 | Buschke |
| 4,779,199 A | 10/1988 | Yoneda et al. | | 5,231,990 A | 8/1993 | Gauglitz |
| 4,782,511 A | 11/1988 | Nemec et al. | | 5,243,515 A | 9/1993 | Lee |
| 4,789,928 A | 12/1988 | Fujisaki | | 5,249,044 A | 9/1993 | Von Kohorn |
| 4,796,639 A | 1/1989 | Snow et al. | | 5,251,126 A | 10/1993 | Kahn et al. |
| 4,799,156 A | 1/1989 | Shavit et al. | | 5,261,401 A | 11/1993 | Baker et al. |
| 4,799,199 A | 1/1989 | Scales, III et al. | | 5,262,943 A | 11/1993 | Thibado et al. |
| 4,803,625 A | 2/1989 | Fu et al. | | 5,265,888 A | 11/1993 | Yamamoto et al. |
| 4,835,372 A | 5/1989 | Gombrich et al. | | 5,266,179 A | 11/1993 | Nankai et al. |
| 4,838,275 A | 6/1989 | Lee | | 5,275,159 A | 1/1994 | Griebel |
| 4,846,797 A | 7/1989 | Howson et al. | | 5,277,197 A | 1/1994 | Church et al. |
| 4,853,521 A | 8/1989 | Claeys et al. | | 5,282,950 A | 2/1994 | Dietze |
| 4,858,354 A | 8/1989 | Gettler | | 5,295,491 A | 3/1994 | Gevins |
| 4,858,617 A | 8/1989 | Sanders | | 5,299,121 A | 3/1994 | Brill et al. |
| 4,890,621 A | 1/1990 | Hakky | | 5,301,105 A | 4/1994 | Cummings, Jr. |
| 4,894,777 A | 1/1990 | Negishi et al. | | 5,304,112 A | 4/1994 | Mrklas et al. |
| 4,897,869 A | 1/1990 | Takahashi | | 5,304,468 A | 4/1994 | Phillips |
| 4,899,839 A | 2/1990 | Dessertine et al. | | 5,307,263 A | 4/1994 | Brown |
| 4,903,201 A | 2/1990 | Wagner | | 5,309,919 A | 5/1994 | Snell et al. |
| 4,907,973 A | 3/1990 | Hon | | 5,321,009 A | 6/1994 | Baeder et al. |
| 4,916,441 A | 4/1990 | Gombrich | | 5,325,288 A | 6/1994 | Satou |
| 4,926,325 A * | 5/1990 | Benton et al. .................... 705/39 | | 5,329,459 A | 7/1994 | Kaufman et al. |
| 4,931,934 A | 6/1990 | Snyder | | 5,329,608 A | 7/1994 | Bocchieri et al. |
| 4,933,873 A | 6/1990 | Kaufman et al. | | 5,331,549 A | 7/1994 | Crawford, Jr. |
| 4,933,876 A | 6/1990 | Markoff et al. | | 5,333,981 A | 8/1994 | Pronovost et al. |
| 4,950,246 A | 8/1990 | Muller | | 5,335,338 A | 8/1994 | Proesel |
| 4,950,264 A | 8/1990 | Osborn, III | | 5,339,821 A | 8/1994 | Fujimoto |
| 4,953,552 A | 9/1990 | DeMarzo | | 5,341,291 A | 8/1994 | Roizen et al. |
| 4,958,632 A | 9/1990 | Duggan | | 5,343,239 A | 8/1994 | Lappington et al. |
| 4,958,641 A | 9/1990 | Digby et al. | | 5,344,324 A | 9/1994 | O'Donnell et al. |
| 4,967,756 A | 11/1990 | Hewitt | | 5,357,427 A | 10/1994 | Langen et al. |
| 4,974,607 A * | 12/1990 | Miwa ............................ 600/483 | | 5,366,896 A | 11/1994 | Margrey et al. |
| 4,977,899 A | 12/1990 | Digby et al. | | 5,368,562 A | 11/1994 | Blomquist et al. |
| 4,978,303 A | 12/1990 | Lampbell | | 5,371,687 A * | 12/1994 | Holmes et al. .................. 710/72 |
| 4,978,335 A | 12/1990 | Arthur, III | | 5,375,604 A | 12/1994 | Kelly et al. |
| 4,979,509 A | 12/1990 | Hakky | | 5,377,100 A | 12/1994 | Pope et al. |
| 5,007,429 A | 4/1991 | Treatch et al. | | 5,377,258 A | 12/1994 | Bro |
| 5,009,645 A | 4/1991 | Silver et al. | | 5,390,238 A | 2/1995 | Kirk et al. |
| 5,016,172 A | 5/1991 | Dessertine | | 5,399,821 A | 3/1995 | Inagaki et al. |
| 5,019,974 A | 5/1991 | Beckers | | 5,410,471 A | 4/1995 | Alyfuku et al. |
| 5,024,225 A | 6/1991 | Fang | | 5,410,474 A | 4/1995 | Fox |
| 5,025,374 A | 6/1991 | Roizen et al. | | 5,429,140 A | 7/1995 | Burdea et al. |
| 5,034,807 A | 7/1991 | Von Kohorn | | 5,431,690 A | 7/1995 | Schaldach et al. |
| 5,035,625 A | 7/1991 | Munson et al. | | 5,431,691 A | 7/1995 | Snell et al. |
| 5,036,462 A | 7/1991 | Kaufman et al. | | 5,434,611 A | 7/1995 | Tamura |
| 5,049,487 A | 9/1991 | Phillips et al. | | 5,438,607 A | 8/1995 | Przygoda, Jr. et al. |
| 5,050,612 A | 9/1991 | Matsumura | | 5,438,983 A | 8/1995 | Falcon |
| 5,056,059 A | 10/1991 | Tivig et al. | | 5,441,047 A | 8/1995 | David et al. |
| 5,059,394 A | 10/1991 | Phillips et al. | | 5,449,334 A | 9/1995 | Kingsbury |
| 5,065,315 A | 11/1991 | Garcia | | 5,454,721 A | 10/1995 | Kuch |
| 5,068,536 A | 11/1991 | Rosenthal | | 5,454,722 A | 10/1995 | Holland et al. |
| 5,074,317 A | 12/1991 | Bondell et al. | | 5,456,606 A | 10/1995 | McIntyre |
| 5,077,476 A | 12/1991 | Rosenthal | | 5,456,692 A | 10/1995 | Smith, Jr. et al. |
| 5,077,665 A | 12/1991 | Silverman et al. | | 5,458,123 A | 10/1995 | Unger |
| 5,095,798 A | 3/1992 | Okada et al. | | 5,467,269 A | 11/1995 | Flaten |
| 5,104,380 A | 4/1992 | Holman et al. | | 5,471,039 A | 11/1995 | Irwing, Jr. et al. |
| 5,109,414 A | 4/1992 | Harvey et al. | | 5,471,382 A | 11/1995 | Tallman et al. |
| 5,109,974 A | 5/1992 | Beer et al. | | 5,483,276 A | 1/1996 | Brooks et al. |
| 5,111,396 A | 5/1992 | Mills et al. | | 5,488,412 A | 1/1996 | Majeti et al. |
| 5,111,817 A | 5/1992 | Clark et al. | | 5,488,423 A | 1/1996 | Walkingshaw et al. |
| 5,111,818 A | 5/1992 | Suzuki et al. | | 5,497,772 A * | 3/1996 | Schulman et al. .............. 600/347 |
| 5,120,230 A | 6/1992 | Clark et al. | | 5,501,231 A | 3/1996 | Kaish |

| Patent No. | Date | Inventor(s) |
|---|---|---|
| 5,502,636 A | 3/1996 | Clarke |
| 5,502,726 A | 3/1996 | Fischer |
| 5,504,519 A | 4/1996 | Remillard |
| 5,507,288 A * | 4/1996 | Bocker et al. ................. 600/322 |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Magrey et al. |
| 5,633,910 A | 5/1997 | Cohen |
| 5,635,532 A | 6/1997 | Samid |
| 5,640,569 A | 6/1997 | Miller et al. |
| 5,640,953 A | 6/1997 | Bishop et al. |
| 5,642,731 A | 7/1997 | Kehr |
| 5,642,936 A | 7/1997 | Evans |
| 5,651,363 A | 7/1997 | Kaufman et al. |
| 5,651,775 A | 7/1997 | Walker et al. |
| 5,659,691 A | 8/1997 | Durward et al. |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,679,075 A | 10/1997 | Forrest et al. |
| 5,680,590 A | 10/1997 | Parti |
| 5,680,866 A | 10/1997 | Kangas et al. |
| 5,687,322 A | 11/1997 | Deaton et al. |
| 5,687,717 A | 11/1997 | Halpern et al. |
| 5,687,734 A | 11/1997 | Dempsey et al. |
| 5,689,652 A | 11/1997 | Lupien et al. |
| 5,692,906 A | 12/1997 | Corder |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,704,922 A | 1/1998 | Brown |
| 5,710,178 A | 1/1998 | Samid |
| 5,710,918 A | 1/1998 | Lagarde et al. |
| 5,711,297 A | 1/1998 | Iliff |
| 5,714,319 A | 2/1998 | Joutel et al. |
| 5,715,451 A | 2/1998 | Marlin |
| 5,715,823 A | 2/1998 | Wood et al. |
| 5,717,739 A | 2/1998 | Dyer et al. |
| 5,717,913 A | 2/1998 | Driscoll |
| 5,720,733 A | 2/1998 | Brown |
| 5,722,418 A * | 3/1998 | Bro ................. 600/545 |
| 5,727,153 A | 3/1998 | Powell |
| 5,730,124 A | 3/1998 | Yamauchi |
| 5,730,654 A | 3/1998 | Brown |
| 5,732,696 A | 3/1998 | Rapoport et al. |
| 5,732,709 A | 3/1998 | Tacklind et al. |
| 5,734,413 A | 3/1998 | Lappington et al. |
| 5,749,083 A | 5/1998 | Koda et al. |
| 5,752,234 A | 5/1998 | Withers |
| 5,754,740 A | 5/1998 | Fukuoka et al. |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,787,295 A | 7/1998 | Nakao |
| 5,791,342 A | 8/1998 | Woodard |
| 5,792,117 A | 8/1998 | Brown |
| 5,793,969 A | 8/1998 | Kamentsky et al. |
| 5,794,219 A | 8/1998 | Brown |
| 5,794,251 A | 8/1998 | Watanabe et al. |
| 5,796,393 A | 8/1998 | MacNaughton et al. |
| 5,799,318 A | 8/1998 | Cardinal et al. |
| 5,800,458 A | 9/1998 | Wingrove |
| 5,802,494 A | 9/1998 | Kuno |
| 5,802,534 A | 9/1998 | Hatayama et al. |
| 5,806,057 A | 9/1998 | Gormley et al. |
| 5,810,747 A | 9/1998 | Brudny et al. |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,933,136 A | 8/1999 | Brown |
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |

| | | |
|---|---|---|
| 6,068,615 A | 5/2000 | Brown et al. |
| 6,095,985 A | 8/2000 | Raymond et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown et al. |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,334,778 B1 * | 1/2002 | Brown .......... 434/258 |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,513,532 B2 | 2/2003 | Mault et al. |
| 2002/0019748 A1 | 2/2002 | Brown |
| 2003/0126593 A1 * | 7/2003 | Mault .......... 725/10 |
| 2004/0106855 A1 * | 6/2004 | Brown .......... 600/301 |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0251520 | 7/1988 |
| EP | 0286456 | 10/1988 |
| EP | 0320749 | 2/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 11/1994 |
| EP | 676709 | 10/1995 |
| EP | 680727 | 11/1995 |
| EP | 761160 | 3/1997 |
| EP | 08131551 | 12/1997 |
| GB | 2218831 | 11/1989 |
| GB | 2225637 | 6/1990 |
| JP | 54005758 | 1/1979 |
| JP | 54146633 | 11/1979 |
| JP | 62226278 | 10/1987 |
| JP | 5155024 | 6/1993 |
| JP | 5266002 | 10/1993 |
| JP | 1995407095963 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

Nunziata, S.; "Nintendo, Sony Game on CD-ROM"; Billboard; Oct. 31, 1992; p. 86.*

Hutchens, B.; "Nintendo Cartridge Expands Game Boy Play to TV Screen"; The News Tribune; Tacoma, Washington; Jun. 25, 1994; p. H.2.*

Patton, R.; "LSI Logic ASIC Powers Sony Playstation"; Electronics; Jun. 27, 1994; p. 12.*

"Blood Glucose Monitors", *Portable Health Device*, (1988), vol. 17(9), pp. 253-271.

"Central Fetal Monitoring Systems ewith Optical Disk Storage", *New Technology Brief*, (Nov./Dec. 1988), vol. 2, No. 6, pp. 249-251.

"European Search Report", From 6858P005EP, (Mar. 27, 1998).

"How Flash Memory Works", *Internet printout of URL address*: http://www.howstuffworks.com/flash-memory4.htm. (Sep. 28, 2002),2 pages.

"Introducing the Next Generation of About Your Diabetes", *U.S. Pharmacopcial Convention and American Diabetes Association*, (1993).

"The description of the Tandy Radio Shack TRS-80 Model 100/102 device avaliable at http://www.old-computers.com/museum/computer.asp?c=233", *World Wide Web*, (Feb. 13, 2004),1-3.

Anonymous, "Health Hero network, inc. Receives First-Ever FDA Clearance for Connection Medical Devices to Internet", *PR Newswire*, (Dec. 2, 1999),3 pages.

Billard, A., et al., "Telematic Transmission of Computerized Blood Glucose Profiles for IDDM Patients", *Diabetes Care*, (Feb. 1991),vol. 14, No. 2, pp. 130-134.

Bower, "Brain Clues to Energy-efficient Learning", *Science News*, (Apr. 1992),v141; p. 215(1); Dialog: File 647, Acct# 12123949.

Bruce, "Health Hero Network CEO, CNNfn", *Digital Jam*, (Dec. 1, 1999),3 pages.

Bruce, et al., "The Effects of Sympathetic Nervous System Activation and Psychological Stress . . . ", *Diabetologia*, (1992),. ; ; 35 (9); 835-843; Dialog: File 5, Acc# 9629427.

Brunetti, P., et al., "A Simulation Study on a Self-Tuning Portable Controller of Blood Glucose", *The International Journal of Artifical Organs*, (1993),vol. 16, No. 16, pp. 51-57.

Caprihan, A., et al., "A Simple Microcomputer for Biomedical Signal Processing", *IECI '78 Annual Conference Proceedings on Industrial Applications of Microprocessors*, (Mar. 20, 1978),18-23.

Cheng, Joe H., "PCT Search Report", (Jan. 11, 1996).

Douglas, A. S., et al., "Hand-Held Glucose Monitor and Recorder", *Proceedings of the Annual International Conference of the IEEE Engineering in Medicine and Biology Society*, New Orleans, LA,(Nov. 1988),pp. 747-748.

Fabietti, P. G., et al., "Wearable System for Acquisition, Processing and Storage of the Signal from Amperometric Glucose Sensors", *The International Journal of Artificial Organs*, (1991),vol. 14, No. 3, pp. 175-178.

Finston, "Parent + Teacher = Healthy Child", *Diabetes Forecast*, (Apr. 1994),v47 n9; p. 26(5); Dialog: file 149, Acc# 15804228.

Fox, "Not My Type: Type B Behavior, Type I Diabetes Plus Stress Equals Blood Sugar Blues", *Health*, (Mar. 1988),v20 n3; pp. 22(1); Dialog: File 149, Acc# 06397959.

Frieberger, Paul, "Video Game Takes on Diabetes Superhero "Captin Novolin" Offers Treatment Tips", *San Francisco Examiner*, (Jun. 26, 1992),Fourth Edition, Business Section B1.

Giuffrida, Antonio, et al., "Should We Pay the Patient? Review of Financial Incentives to enhance Patient compliance", *Biomedical Journal*, (1997),vol. 315, pp. 703-707.

Hauben, Jay R., "A Brief History of the Cleveland Free-Net", avaliable at http://www.ais.org/~irh/acn7-1.a09.html, (1995),pp. 1-4.

Hauser, Thomas, et al., "Will Computers Replace or Complement the Diabetes Educator?", *The Medical Journal of Australia*, (Oct. 5, 1992),vol. 157, 489-491.

Horio, Hiroyuki, et al., "Clinical Telecommunication Network System for Home Monitoring", *Medical & Biological Engineering & Computing*, (Mar. 1994),vol. 32, 227-230.

Hunter, "Technological Advances in Bedside Monitoring: Biosensors", *Archives and Laboratory Medicine*, (Jul. 1987),pp. 633-636.

Kauffmann, Francine, et al., "Epidemiological Study of the Genetics and Environment of Asthma, Bronchial Hyperresponsiveness and Atopy", *Am. J. Respir. Crit. Care Med.*, (1997),vol. 156, pp. S123-S129.

Kaufman, Steven, "B., The Learning Game", *Nation's Business*, (Nov. 1993).

Kuykendall, V G., et al., "Assessment of Self-Monitored Blood Glucose results Using a Reflectance Meter with Memory and Microcomputer", *Symposium on Computer Applications in Medical Care*, (Jan. 1981),vol. 70, pp. 98-102.

Lacyk, John, "PCT Search Report", (Jun. 12, 1997).

Latman, N. S., "Evaluation of Electronic, Digital Blood Glucose Monitors", *Biomedical Instrumentation and Technology*, (1991),vol. 25, No. 1, 43-49.

Laughton, Miles E., "A Portable Microcomputer for Long-Term Physiological Monitoring in the Home and Work Environment", *Medical Monitoring in the Home and Work Environment*, (1990),pp. 47-57.

Leyerle, Beverly J., et al., "The PDMS as a Focal Point for Distributed Patient Data", *International Journal of Clinical Monitoring and Computing*, (1988),vol. 5, pp. 155-161.

Makikawa, M., et al., "Microprocessor-Based Memory Device for Ambulatory Heart Rate and Physical Activity Recording", *Methods of Information in Medicine*, (1994),vol. 33, No. 1, pp. 94-96.

Marsh, David G., "Approaches Toward the Genetic Analysis of Complex Traits Asthma and Atopy", *Am. J. Respir.Crit.Care.Med.*, (1997),vol. 156, pp. S-133-S138.

Martinez, Fernando D., "Complexities of the Genetics of Asthma", *Am. J, Respir. Crit. Care Med.*, (1997),vol. 156, pp. S117-S122.

Mazzola, et al., "Video Diabetes: A Teaching Tool for Children with Insulin-Dependent Diabetes", *Proceedings—7th Annual Symposium on Computer Applications in Medical Care; Washington, DC; Dialog:*, (Oct. 1983),File 8, Acc# 01624462.

Meissner, et al., "Building an Integrated Clinical and Research Network", *Proceedings of the SPIE*, (Oct. 24, 1995),vol. 2618, p. 92 99.

Moore, "New Applications Break Through Storage Boundaries", *Computer Technology Review*, (Oct. 1999),vol. 19, No. 10, p. 1.

Pfeiffer, E. F., "The Glucose Sensor: The Missing Link in Diabetes Therapy", *Hormone and Metabolic Research*, (1990),vol. 24, Suppl., pp. 154-164.

Poitout, V., et al., "A Glucose Mointoring System for On Line Estimation in Man of Blood Glucose Concentration Using a Miniaturized Glucose Sensor Implanted in the Subcutaneous Tissue and a Wearable Control Unit", *Diabetologia*, (1993),vol. 36, pp. 658-663.

Potter, David, "Fundamentals of PC-Based Data Acquisition", *Sensors*, (Feb. 1994),pp. 12-20.

Reis, Howard, "Telemedicine: Transmitting Expertise to the Point of Care", *Proceedings: Toward an Electronic Patient Record*(1997),pp. 248-256.

Roberts;, "Diabetes and Stress: A Type A Connection?", *Psychology Today*, (Jul. 1987),vol. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", *Archives of Pathology and Laboratory Medicine*, (Jun. 1993),vol. 117, pp. 611-617.

Schenkels, P., "Supplementary European Search Report", Application No. EP 97 92 2716,(Mar. 11, 2002).

Schork, Nicholas J., "Genetics of Complex Disease", *Am. J. Respir. Crit. Care Med.*, (1997), vol. 156, pp. s103-S109.

Schrezenmeir, J., et al., "Computer Assisted Insulin Dosage Adjustment—Perspective for Diabetes Control", *Hormone and Metabolic Research, Supplement Series*, (1990),vol. 24, pp. 116-123.

Shandle, Jack, "Who Will dominate the desktop in the 90's?", *Electronics*, (Feb. 1990),pp. 48-50.

Shults, Marc C., et al., "A Telemetry-Instrumentation System for Monitoring Multiple Subcutaneously Implanted Glucose Sensors", *IEEE Transactions on Biomedical Engineering*, (Oct. 1994),vol. 41, No. 10, pp. 937-942.

Soeldner, J. S., "Treatment of Diabetes Mellitus by Devices", *The American Journal of Medicine*, (Jan. 1981),vol. 70, 183-194.

Updike, Stuart J., et al., "Laboratory Evaluation of New Resusable Blood Glucose Sensor", *Diabetes Care*, (Nov./Dec. 1988),vol. 11, No. 10, pp. 801-807.

Vallera, D. A., et al., "Accuracy of Portable Blood Glucose Monitoring", *American Journal of Clinical Pathology*, (1991),vol. 95, No. 2, pp. 247-252.

Voelker, Rebecca, "Shoe Leather Therapy is Gaining on TB", *Jama*, (Mar. 13, 1996),vol. 275, 743.

Wyatt, J. C., "Clinical Data Systems, Part 2: Components and Techniques", *Lancet*, (Dec. 1994),vol. 344, No. 8937, pp. 1609-1614.

Yoshizawa, Daisuke, et al., "The Development of a Data Processing System with Personal Computer MSX Standard System for Flow Injection Analysis", *Journal of Flow Injection Analysis*, (1988),V. 5, No. 2. pp. 101-110.

"AdOptimizer—Ad Management Software For Websites", Newsnytes, pNEW10040041, Oct. 4, 1996.

"Cathay Pacific Airways—USA receives more then 1,300 bids during first five days of CyberAuction"; Business Wire, Oct. 18, 1995, p10181119.

"Cathay Pacific Airways—USA to Hold First-Ever Internet CyberAuction; CyberTravelers Can Bid for 50 Business Class Round Trips to Hong Kong—No Minimum Bid"; Business Wire; p9261084; Sep. 26, 1995; Dialog: File 148, Acc#08167091.

"Digital Doggie"; retrieved from URL http://www.virtualpet.com/vp/farm/gigapet/doggie.htm Apr. 23, 2000.

"Future of the Virtual Pet Industry," 1997 [retrieved on Apr. 23, 2000], Retrieved from <URL:www.virtualpet.com/vp/future/future.htm>.

"Giga Farm"; retrieved from URL http://www.virtualpet.com/vp/farm/gigapet/gpfarm/gpfarm.htm Apr. 23, 2000.

"Giga Pets," 1997 [retrieved on Apr. 23, 2000], Retrieved from <URL:www.virtualpet.com/vp/farm/gigapet/gigapet.htm>.

"Nano Baby Instructions"; retrieved from file://C:\My Documents\Nano Baby Instructions.htm Apr. 23, 2000.

"Nano Fighter Pets"; retrieved from URL http://www.virtualpet.com/vp/farm/nano/nfighter.htm Apr. 23, 2000.

"New Horizons teams with Duke, Real Media"; The Seybold Report on Desktop Publishing, v10 n12 p. 24(1), Aug. 12, 1996.

"Onsale Joins Fray as Online Shopping Picks Up Speed: Internet Booms"; Computer Reseller News; Jun. 5, 1995; p. 73; Dialog: File 16, Acc#05649796.

"Onsale Onsale Brings Thrill of Auctions and Bargain Hunting Online; Unique Internet retail service debuts with week-long charity auction for The Computer Museum in Boston", May 24, 1995; Dialog Abstract: File 610, Acc#0489267.

"Playmates Toys deals knockout blow to virtual pet competitors with introduction of Nano Fighter™ for Boys"; New Nano Pet Fighting Pet Press Release; retrieved from URL http://www.virtualpet.corn/vp/farm/nano/nfightpr.htm Apr. 23, 2000.

"Playmates Toys leads Americas virtual pet craze into its next generation by introducting talking Nano Pals"; Talking Nano Pet Press Release; Nov. 18, 1997; retrieved from URL http://www.virtualpet.com/vp/farm/nano/talkn/tnpress.htm on Apr. 23, 2000.

"Putting the Lot on the Net", Antique Collector, vol. 66, Issue 9, p. 26, Downloaded from Corporate Resource Net, Nov./Dec. 1995.

"Talking Nano Puppy"; retrieved from URL http://www.virtualpet.com/vp/farrn/nano/talkn/talkn.htm Apr. 23, 2000.

"Tamagotchi," 1997 [retrieved on Apr. 23, 2000], Retrieved from <URL:www.virtualpet.com/vp/farm/lleg/lleg.htm>.

"Theme Hospital," product review 1996 [retrieved Apr. 21, 2000], Retrieved from <URL:www.vigilante.co.uk/ep/misc/hospital.htm>.

"Towards a partnership of care", M2 Presswire, Jun. 14, 2000.

"Virtual Pet Product Reviews," 1997 [retrieved on Apr. 23, 2000], Retrieved from <URL:www.virtualpet.com/vp/farm/reviews/reviews,htm>.

"Virtual Tomagutchi,"1998 [retrieved Apr. 23, 2000], Retrieved from <URL:www.sttf.org/english/action/tomagutchi.html>.

"Who Will Dominate the Desktop in the 90's?", Jack Shandle, Electronics, Feb. 1990, pp. 48-50. (3 pages).
Adilman; "Videogames: Knowing the Score"; Creative Computing; v9; p. 224(5); Dec. 1983; Dialog: File 148, Acc# 01891055.
Bai, "Design of home healthcare network", IEEE 1997 pp. 1657-1658.
Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.
DigiPet Instruction Manual, 1997.
Edelson; "Fashion Reevaluates Flickering Fortunes of TV Home Shopping"; WWD; v170 n87; p. 1(3); Nov. 8, 1995; Dialog: File 148, Acc#08289119.
Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.
Furnham et al., "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.
Gardner, et al.; "Comprehension and Appreciation of Humorous Material Following Brain Damage"; Brain; Sep. 1975; 98(3); pp. 399-412; Dialog: File 153, Acc#02859983. (14 pages).
Gauntlet (for PC) rulebook by Mindscape Inc. (Gauntlet by Apple);1985.
Gordon; "Auctions Become High Tech"; Dealer Business; v29 n7; p.21(4); Mar. 1995; Dialog: File 148, Acc#07862519.
Howey, et al., "A Rapidly Absorbed Analogue of Human Insulin"; Diabetes, vol. 43, Mar. 1994, pp. 396-402. (7 pages).
Hutheesing, Nikhil, "An on-line gamble", Forbes, v157 n10 p. 288(1), May 20, 1996.
Jaffrey et al.; "PIN: An Associated Protein Inhibitor of Neuronal Nitric Oxide Synthase"; Science; vol. 274; Nov. 1, 1996; Ref: XP 002050141.
Jimison et al., "Patient-Specific explanation in models of chronic disease", Revised Feb. 1992 Artificial Intelligence in Medicine 4 (1992) 191-205.
Jones, Chris, "Microsoft readies DocObject; technology will allow document editing in Web browsers", InfoWorld, v18 n18 p. 48(1), Apr. 29, 1996.
Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.
Lachnit, Carroll, "Hawkin's Online Auction", Photo District News, vol. 16, Issue 1, p. 18, Jan. 1996.
Luebke, Cathy, "Barrett-Jackson Auction Turns High-Tech", Business Journal, vol. 16, Issue 12, pp. 11, Jan. 19, 1996.
M.U.L.E. rulebook by Electronic Arts, 1983.
Marx, Wendy, "More than just the Scores: ESPNET SportsZone is a model for expanding brand names online", InformationWeek, n576 p. 61(2), Apr. 22, 1996.
McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.
Mims; "Psychological Testing"; Computers & Electronics; v23; p. 22(6); Feb. 1985; Dialog: File 47, Acc# 2654858.
Nano Page, 1997 [retrieved on Apr. 23, 2000], Retrieved from <URL:www.virtualpet.com/vp/farm/nano/nano.htm>.
O'Donnell; "Alan's At It Again"; Bond Buyer; v309 n29448; p. 1(3); Jul. 21, 1994; Dialog: File 148, Acc#07478152.
Octogotchi Instruction Manual, 1997. Dino-Kun Instruction Manual, 1997.
Polson, Gary "Recent Developments and Trends in Keychain Virtual Pets," 1997 [retrieved on Apr. 23, 2000], Retrieved from <URL:www.virtualpet.com/vp/future/trends1a.htm>.
Research project launched to improve health of America's communities; new Disney community in Florida is focus of program. Business Wire, p. 10011142. Oct. 1, 1996.
Results of the world's first on-line auction, http://www.christies.com.
Ro__Auction Auctioneers Property Database System and Ro__Auction Auctioneers Accounting System; Ro-Auction features; Dec. 4, 1995.
Save the earth artrock auction, http://www.commerce.com.saveearth. Auction Web, http://www.ebay.com.
Schement, "An Intelligent Controller for Neurophysiological Experiments," Proceeding of the Annual Symposium on Computer Based Medical Systems, Durham, Jun. 14-17, 1992, p. 528, line 1—p. 529, line 21.
Siegmann;"Nowhere to Go but Up"; PC Week; v12 n42, p. A5(1); Oct. 23, 1995; Dialog: File 148, Acc#08222496.
Skolnick et al. "Simultaneous Analysis of Multiple Polymorphic Loci Using Amplified Sequence Polymorphisms (ASPs)"; Genomics. 2: 273-279.
Spitzer et al.; "The moderating effect of age on self-care"; Western Journal of Nursing Research, v18, n2, p. 136(13), Apr. 1996.
Telemedicine Provides Two-Way Computer Link for Parents of Very Premature Infants. PR Newswire. p. 1007NEM034. Oct. 7, 1996.
United Healthcare's Optum Division goes online to better health by announcing a unique internet application. PR Newswire, p. 0801MNTH004. Aug. 1, 1996.
Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.
Wilkins, Aaron. "Expanding Internet access for health care consumers", Health Care Management Review, Summer, Jul. 1999, 24-30.
Alere Medical Inc 's First Supplemental Response to Plaintiff's Amended Interrogatory No. 2. Jun. 20, 2008.
U.S. Appl. No. 90/010,053—Order Granting Request for Ex Parte Reexamination, Jan. 18, 2008.
U.S. Appl. No. 90/009,237__Request__for__Re-examination__5601435__Aug. 1, 2008.

* cited by examiner

*Primary Examiner* — Kang Hu
(74) *Attorney, Agent, or Firm* — Maginot, Moore & Beck

(57) ABSTRACT

The invention describes a system and method for allowing an individual to view an educational program remotely. In the preferred embodiment, the invention is used as a healthcare education system. The system comprises a file server which is connected to a database holding the educational programs. A remote interface connected to the file server allows an administrator to assign educational programs to an individual. The remote interface also includes a memory card writer which records the individual's identification code and the address of the file server on a memory card. The individual is given the memory card to take home. When the individual places the memory card in the memory card reader of a multimedia processor, the processor uses the file server address to automatically connect to the file server. The file server receives the individual's identification code from the processor, retrieves the corresponding educational program from the database, and sends the program to the processor to be displayed. After the individual has watched the educational program, completion data in the form of the date and time the program was watched, or the individual's response, is sent from the multimedia processor to the file server. The completion data can then be viewed by the administrator on a report screen.

51 Claims, 8 Drawing Sheets

PROGRAM ASSIGNMENT SCREEN — 150

AVAILABLE PROGRAMS:  STUDENTS:

- [X] DIABETES AND EXERCISE — 166, 168  [X] DAN LINDSEY
- [ ] FOOD EXCHANGES AND DIET  [ ] MARK SMITH — 178
- [ ] BLOOD GLUCOSE MONITORING  [ ] DEAN JONES

[ADD NEW PROGRAM] [SAVE NEW LISTING] [ADD NEW PATIENT] — 174
176 — [ASSIGN PROGRAM] — 170  [DELETE PROGRAM] — 172

REPORT SCREEN — 152

| STUDENT | ASSIGNED PROGRAM | PROGRAM COMPLETED | RESULTS/SCORE |
|---|---|---|---|
| DAN LINDSEY | DIABETES AND EXERCISE | MAY 1, 1997, 5:22 PM | COMPLETED |
| MARK SMITH | FOOD EXCHANGES AND DIET | MAY 3, 1997 3:54 PM | 79 |
| DEAN JONES | BLOOD GLUCOSE MONITORING | NOT COMPLETED | N/A |

FIG. 4

Thank you for watching "Living With Diabetes", brought to you by Acme Pharmaceuticals. Please answer the following questions by pushing the numbered button on your remote control which corresponds to the best answer.

A. Do you visit your doctor regularly?
   1 - yes     2 - sometimes     3 - no

B. Do you monitor your sugar (glucose) intake?
   1 - yes     2 - sometimes     3 - no C. Do you exercise regularly?
   1 - yes     2 - sometimes     3 - no

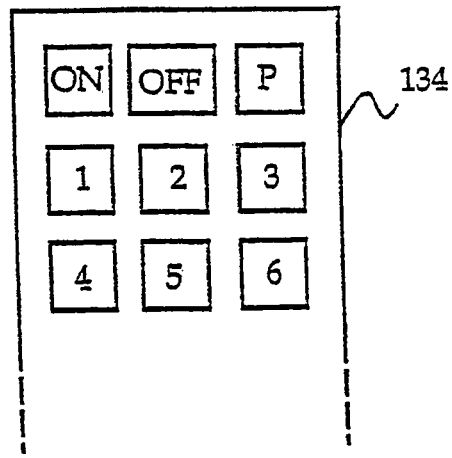

FIG. 5

SYSTEM AND METHOD FOR MONITORING A PHYSIOLOGICAL CONDITION

PRIORITY CLAIM

This application is a Continuation of application Ser. No. 09/971,785, filed Oct. 4, 2001, now abandoned, which is a Continuation of application Ser. No. 09/119,546 filed Jul. 20, 1998, now U.S. Pat. No. 6,330,426 B2, which is a Continuation-In-Part of application Ser. No. 08/953,883 filed Oct. 20, 1997, now abandoned, which is a Continuation-In-Part of application Ser. No. 08/757,129 filed Dec. 3, 1996, now U.S. Pat. No. 6,144,837, which is a Continuation-In-Part of U.S. application Ser. No. 08/334,643, filed on Nov. 4, 1994, now U.S. Pat. No. 5,601,435; and the application Ser. No. 09/119,546 filed Jul. 20, 1998, now U.S. Pat. No. 6,330,426 B2, is also a continuation of application Ser. No. 08/958,786, filed Oct. 29, 1997, now U.S. Pat. No. 5,913,310, which is a Continuation-In-Part of application Ser. No. 08/857,187, filed May 15, 1997, now U.S. Pat. No. 5,918,603, which is a Divisional of application Ser. No. 08/247,716, filed May 23, 1994, now U.S. Pat. No. 5,678,571. All of the above applications are hereby incorporated by reference.

All of the above applications are herein incorporated by reference.

FIELD OF THE INVENTION

The present invention generally relates to remote education systems. More particularly, this present invention relates to a system and method of remote health education in which an individual is provided with a memory card capable of being placed in a multimedia processor to automatically access selected educational health programs.

BACKGROUND OF THE INVENTION

One of the biggest problems many healthcare providers face is their patients' lack of knowledge. Patients may lack knowledge on basic preventative measures, such as why they should exercise, eat right, and not smoke. Patients may also lack knowledge on conditions or diseases they do have, such as how to measure their blood glucose levels if they are diabetic. This lack of knowledge is a problem for healthcare providers because patients who do not know how to take care of themselves are ill more frequently. Thus, they must visit their doctors more often, sometimes incurring additional costs for hospital stays or laboratory tests. This results in greater fees for the patient, his or her insurance company, and often the taxpayers.

An example of this problem is seen in some diabetes patients. Diabetic patients must regularly receive insulin shots and adhere to a specific diet in order to control their blood glucose levels. Unfortunately, some diabetic patients do not understand all the reasons why they should have regular insulin shots or why they should or should not eat certain foods. In addition, many diabetic patients are unaware of the health consequences should they not follow their treatment plan. As a result, such patients are sicker and require more healthcare than those patients who understand all aspects of their diseases. Sicker patients require more healthcare, which is expensive and time-consuming for healthcare professionals, insurance companies, and the patients themselves.

One way this problem is handled is by increasing the amount of education patients receive about their lifestyle choices and/or their diseases. When patients know what they need to do to stay healthy, they are less inclined to visit their doctors as frequently. In addition, if patients understand the health problems that will result from not taking care of themselves, they will be more likely to follow their prescribed treatments.

Educational forms range from pamphlets in a doctor's office to radio announcements to television shows. Paper-based educational material is cheap, easy to produce, and easy to distribute. Unfortunately, pamphlets or articles are limited to words and pictures and are usually quite boring, which makes it unlikely that patients will enjoy and remember reading them. Radio announcements and television shows are more lively and entertaining, but they are broadcast to the general public. Thus they cannot be customized to a particular patient.

Due to technological advances, patients can now be educated using CD-ROMs, the Internet, and multimedia processors. U.S. Pat. No. 5,307,263 by the present inventor discloses a modular, microprocessor-based health monitoring system. The hand-held unit has a display screen, a control button pad, interchangeable program cartridges, and sensors for monitoring a variety of healthcare data. The program cartridges include motivational and educational material related to use of the device, including step-by-step instructions. Acquired data may be transmitted to a data management unit via an interface cable, or to a clearing house via telephone lines. A program cartridge for monitoring glucose levels and a glucose sensor is disclosed for the purpose of caring for children with diabetes.

U.S. Pat. Nos. 5,597,307 and 5,624,265 by Redford and Stem describe an educational system and apparatus aimed at children which also uses a multimedia processor. This invention comprises a remote control located in a book or other printed publication. A child can read the book while watching the display generated by the multimedia processor, and then press the buttons in the remote control book to alter what he sees.

None of the above education systems allow an individual to automatically access assigned educational programs remotely. The inventions described above provide general educational programs which are not tailored to any one individual. Neither system provides confirmation that an individual has completed the educational program. Neither system allows a healthcare provider nor teacher to easily custom-design which educational programs a patient or individual is to view. Finally, neither system provides a patient or individual access to an unlimited number of educational programs.

Virtually everyone in the modern world is touched by the high cost of health care. With rising costs, fewer and fewer people can afford an optimal level of contact with a physician for treatment of health conditions or preventative care. This situation may lead many members of the population who are in need of health care to believe they cannot afford it. These persons are less likely to seek proper health care when needed.

Further, despite great advances in the field of medicine, there may still be some members of the population who feel threatened by or who harbor a distrust or fear of health care professionals or institutions, for any number of reasons. These persons are also less likely to seek proper health care when needed.

The two factors mentioned above: the high cost of health care and distrust or fear of health care professionals or institutions, may combine in members of the population to prevent such persons from seeking out and obtaining adequate health care.

Therefore, what is needed is a device which can reduce health care costs by performing some functions of a health care professional and at the same time reduce possible distrust of health care professionals and institutions by providing health care functions to a user in a non-threatening manner.

It is an object of the present invention to reduce health care costs by performing some functions of a health care professional.

It is yet a further object of the present invention to achieve the above-mentioned objects through education obtained in an enjoyable and interactive manner.

It is an additional object of the present invention to accomplish the above-mentioned objects in a relatively inexpensive and simple-to-use manner.

It is yet an additional object of the present invention to have the capability to be functionally expanded with interchangeable compact disks further reducing initial cost.

The prior art discloses devices that monitor health related parameters. For example, U.S. Pat. No. 5,307,263 discloses a modular, microprocessor-based, health monitoring system. The hand-held unit has a display screen, a control button pad, interchangeable program cartridges and sensors for monitoring a variety of health care data. The program cartridges may include motivational and educational material related to use of the device, including step-by-step instructions. Acquired data may be transmitted to a data management unit via an interface cable and to a clearinghouse via telephone lines. A program cartridge for monitoring glucose levels and a glucose sensor is disclosed having the purpose of caring for children with diabetes. However, this device has the disadvantage of having a relatively small liquid crystal display screen, a limited ability to process and store data due to its small size, and limited on-time due to its battery power. Because this invention is directed to chronic ailments, its educational capabilities are likely limited to teaching how to use the device and to teaching about those chronic ailments to which it is directed.

Another example is disclosed in U.S. Pat. No. 4,803,625 which discloses a personal health monitor that measures a patient's weight, temperature, blood pressure and ECG waveform. A plurality of monitors may be coupled to a central computer via telephone lines. The central computer may prompt the patients to take medication, measure certain health parameters, supply answers to selected questions or determine patient symptoms based on patient responses to questions. The monitor transmits patient data to the central computer. The central computer compares collected patient data to expected values and triggers an alarm if the data falls outside a predetermined range. A disadvantage of this invention is that communication with a central computer is required in order to implement its educational capabilities. This increases the cost and complexity of the entire system.

Yet another example can be found in U.S. Pat. No. 5,024,225 which discloses a personal health monitor and its enclosure. The object of this invention is to provide an enclosure for a health monitor such as the one described in U.S. Pat. No. 4,803,625, discussed above. A disadvantage of this device is that it requires the use of a standard lap top computer as the processing unit which increases the cost of the device.

None of the above-mentioned patented devices benefit from the enhanced sound, video and memory capabilities of a multimedia processor having a CD-ROM digital memory store and operating with a television set.

OBJECTS AND ADVANTAGES OF THE INVENTION

In view of the above, it is an object of the present invention to provide an individual with a remote education system which can be accessed from the individual's home. It is another object of the invention to provide a remote education system which displays educational programs for an individual. It is another object of the present invention to provide interactive educational programs. Another object of the invention is to provide a remote education system comprising a memory card containing an individual's identification code and the locations of educational programs for the individual to view. It is another object of the present invention to provide confirmation that an individual has completed an educational program. It is another object of the invention to provide a remote education system through the Internet. Yet another object of the present invention is to provide a remote healthcare education system for patients. It is another object of the present invention to allow a healthcare provider to assign educational programs for a patient by using a memory card.

These and other objects and advantages will become more apparent after consideration of the ensuing description and the accompanying drawings.

SUMMARY OF THE INVENTION

The present invention comprises a system and method for remote education using a memory card. The system preferably comprises a database, a file server, a remote interface, a memory card writer, a display unit, a multimedia processor, and a card reader. The file server acts as a central hub of the system, because it is preferably coupled to the database, the remote interface, and the multimedia processor. Accordingly, these three components are capable of being located at long distance from one another. The database preferably stores a plurality of educational programs. Preferably, the remote interface allows an administrator, such as a healthcare provider or educator, to assign an educational program to an individual. The identification code of the individual and a pointer referring to the assigned educational program are preferably stored on memory means of the file server. Preferably, by using the memory card writer, the administrator is capable of recording the individual's identification code and the address of the file server onto the memory card.

After the administrator assigns the particular educational program to the individual, the memory card can be given to the individual. When the individual wishes to view the assigned educational program, the individual simply places the card in the card reader. Preferably, the memory card reader is coupled to or located with the multimedia processor, which in turn is coupled to the file server. Upon receiving the memory card, the multimedia processor preferably sends the individual's identification code to the file server. Preferably, the file server then calls up the assigned educational program from the database. The content of the educational program is sent to the multimedia processor and displayed on a display unit for the individual.

Preferably, the file server is notified when the individual has completed the educational program. Completion data includes the date and time the individual watched the educational program. Further, the completion data can also include responses made by the individual to the educational program. Preferably, the file server records the completion data and then send the completion data to the remote interface for the administrator to review.

In the preferred embodiment of the remote education system, the file server is a web server, the remote interface is an interactive web page, and the communication link is the Internet. An administrator assigns an educational program to the individual by entering the assignment information onto the web page. The assignment information is sent to the web server where it is held. When the individual places the memory card into the card reader, the multimedia processor sends the individual's identification code to the web server, which calls up the educational program from the database. In the preferred embodiment, the database can comprise one or more web servers, which allows the administrator to assign to the individual an unlimited amount of material.

In the preferred embodiment, the memory card is a plastic card with a magnetic information strip, similar to an ordinary credit card. The magnetic strip contains the individual's identification code and the location of the file server. In another embodiment, the memory card comprises a circuit. The circuit contains the individual's identification code and the location of the file server.

The present invention is an electronic health monitoring system. A multimedia processor is a modified CD-ROM multimedia interactive television video game console which comprises a microprocessor, hardware, and software. One or more physiological data monitors are coupled to provide a signal representative of a user's physiological parameter, such as blood pressure, to the multimedia processor through an isolated interface circuit. A hand-held program controller having directional buttons is operated by the user to control the various functions of the multimedia processor. A television is coupled to the multimedia processor to provide sound and a video display based upon output signals from the multimedia processor. A monitor can also be used to provide a display platform.

Interchangeable compact disks (CD-ROM) comprise additional software. The software contained in the interchangeable compact disks enables the system to execute a variety of health related functions, to display high quality moving or still video images and to produce high quality sound accompaniment. For example, the system may monitor a user's electrocardiographic signals and display an ECG waveform and various other parameters, such as heart rate, on the television screen. The system may also interactively provide more detailed or educational information to the user based upon the user's operation of the hand-held program controller and also based upon predetermined software routines and data stored within the system.

BRIEF DESCRIPTION OF THE DRAWINGS

The preferred and alternative embodiments of the present invention are described in detail below with reference to the following drawings.

FIG. 3 is a sample program assignment screen as displayed on the remote interface;

FIG. 4 is a sample report screen as displayed on the remote interface;

FIG. 5 is a sample interactive educational program as displayed by the multimedia processor;

DETAILED DESCRIPTION OF THE PREFERRED EMBODIMENT

The present invention provides a system and method for remotely educating an individual using a memory card. In the preferred embodiment, the invention is used to distribute custom-designed health education programs to patients. However, it is to be understood that the invention is not limited to the healthcare industry. The system and method of the invention may be used for any type of remote education application in any field.

Figure 1:
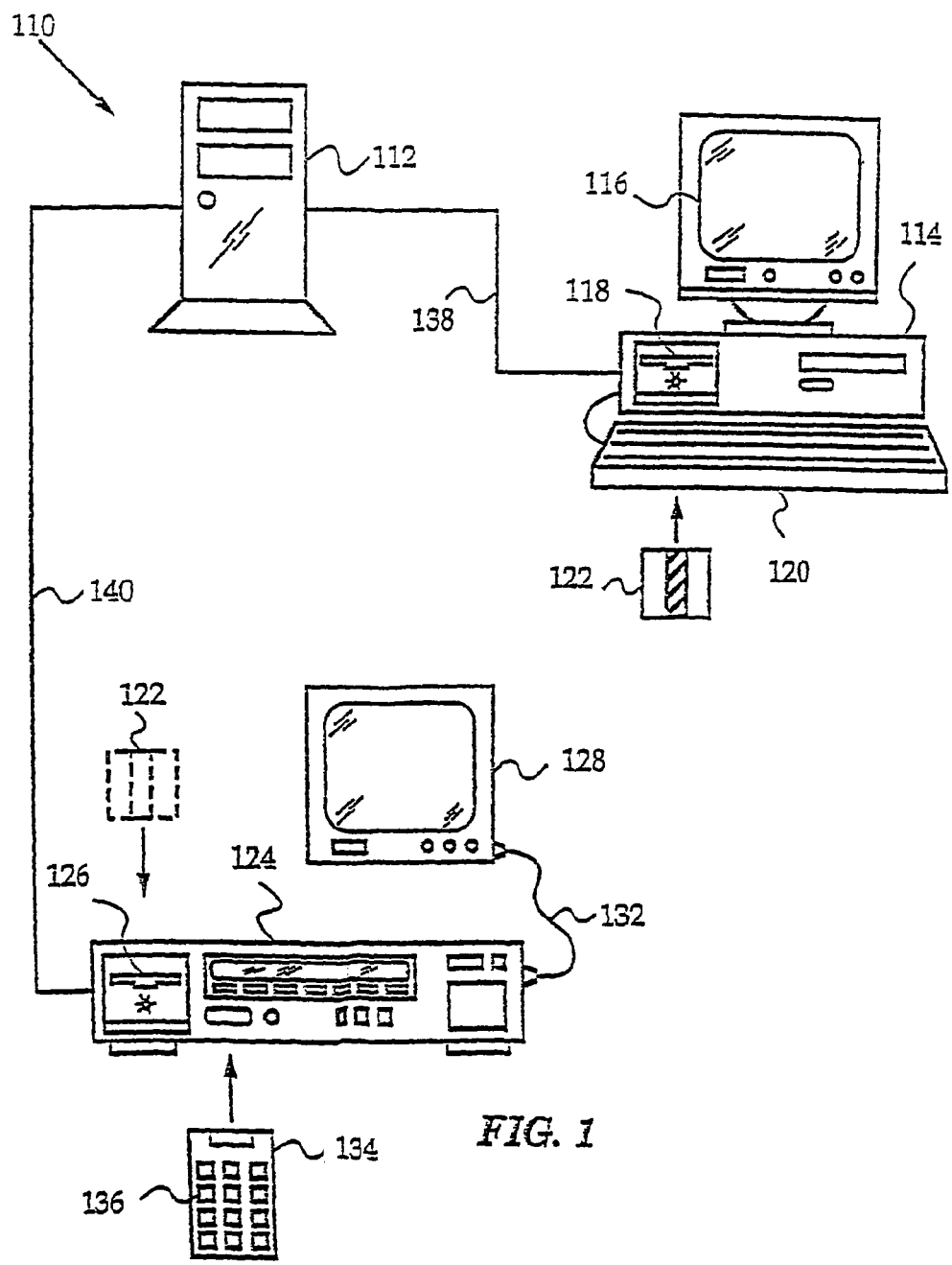
FIG. 1 is a schematic diagram of a remote education system according to a preferred embodiment of the present invention.

The preferred embodiment of the system is shown in FIG. 1. The system 110 comprises a file server 112, which is connected by communication links 138, 130, and 140 to a remote interface 114, a database 148 containing educational programs, and a multimedia processor 124. File server 112 is preferably a world wide web server, remote interface 114 is preferably a web page, and communication links 138 and 130 are preferably the Internet. Remote interface 114 has a display 116 and a keyboard 120, which an administrator can use to assign an educational program to an individual.

Remote interface 114 also contains or is connected to a memory card writer 118. Memory card writer 118 is used to record the individual's identification code and the location of file server 118 on a memory card 118. Preferably, the location of file server 118 is in the form of a uniform resource locator, or URL.

Communication link 140 from file server 112 to multimedia processor 124 is preferably the Internet. However, file server 112 and multimedia processor 124 can also contact each other via wireless communication networks, cellular networks, telephone networks, or any other suitable network. Multimedia processor 124 is also connected by communication link 132 to a display 128, which is used to show educational programs to the individual. Communication link 132 can be any suitable connection means. Display 128 is a standard audiovisual display, such as a television.

Multimedia processor 124 contains or is connected to a memory card reader 126. When memory card 118 is placed in memory card reader 126, the assignment information is sent to file server 112, which retrieves the assigned educational program from database 148. The educational program content is then sent through communication link 40 to multimedia processor 124 and shown on display 128. In addition, microprocessor 124 can also comprise expansion ports to support additional user interfaces and devices, such as keyboards and trackballs, as well as add-on circuits for enhanced sound, video, or processing performance (not shown).

As shown in FIG. 3, input device 134 comprising numerous momentary contact push buttons 136 is used by the individual to control and respond to the educational program. Push buttons 136 represent control functions, such as "on" and "off", as well as numbers, letters, or various commands, such as "yes" and "no". Alternatively, push buttons 136 may be replaced by switches, keys, a touch sensitive display screen, or any other data input device. Input device 134 is a standard wireless communication means which sends command signals to multimedia processor 124 to be processed and executed. However, any communication means which allows input device 134 to connect with multimedia processor 124.

For clarity of illustration, only one database and only one multimedia processor are shown in FIG. 1. It is to be understood that system 110 may include any number of databases for storing any number of educational programs, and any number of multimedia processors for use by any number of individuals.

Figure 2:
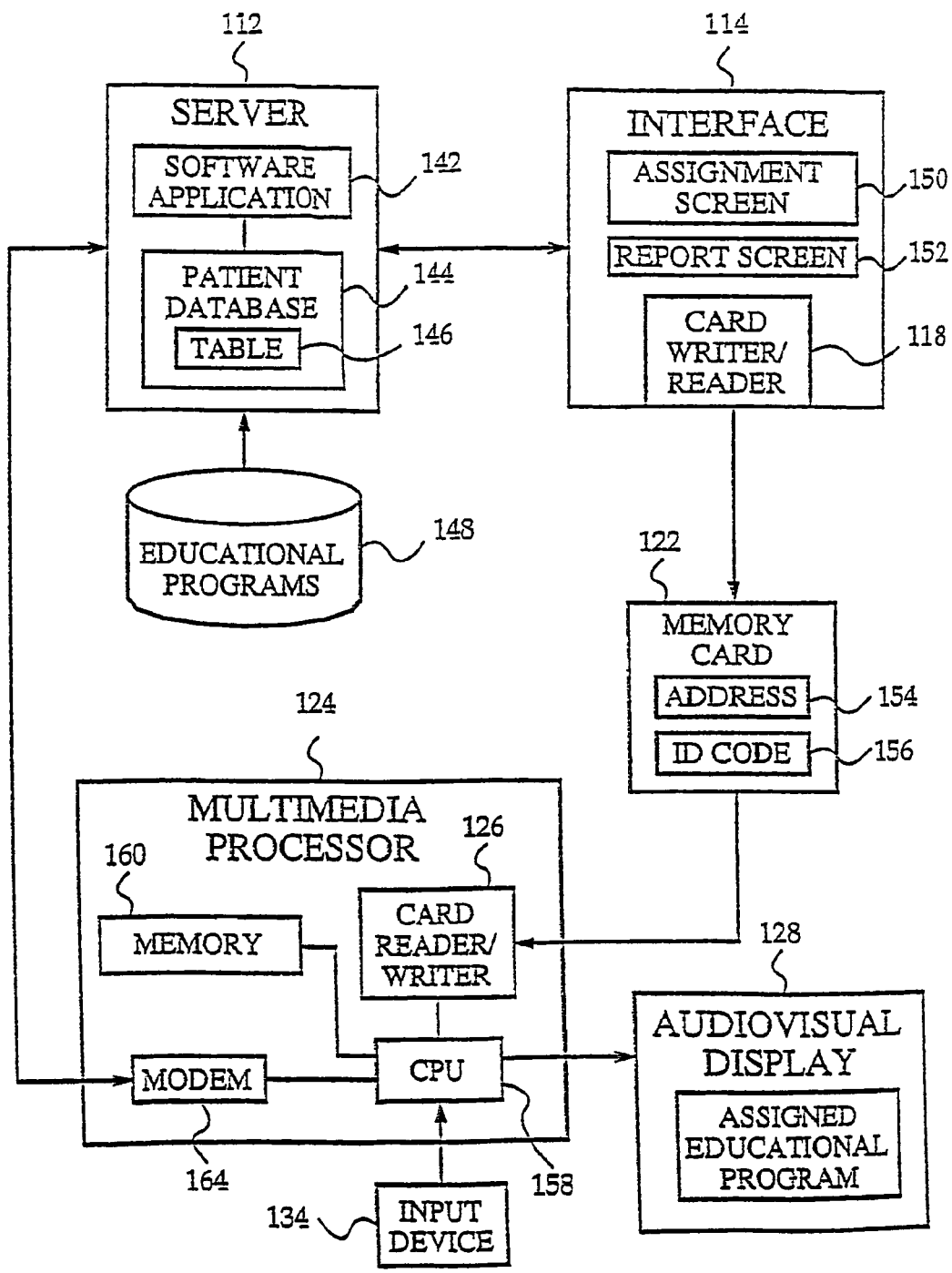
FIG. 2 is a block diagram showing the components of the remote education system and how they are connected, according to FIG. 1.

FIG. 2 shows a detailed block diagram of the preferred embodiment of the invention illustrated in FIG. 1. Server 112 includes a general software application 142 which is used create a database 144 and a patient table 146. Software application 142 is also capable of programming file server 112 to carry out standard commands such as receiving, saving, and transmitting information. Database 144 contains the educational programs 148. Alternatively, database 144 can contain pointers to educational programs 148 which are located in remote databases. The advantage of the pointers is that they allow the healthcare provider to assign any number of educational programs 148, as long as educational programs 148 can be transmitted to multimedia processor 124 and shown on display 28. Thus suitable forms of educational programs 148 include photos, videos, animation, static web pages, interactive web pages, etc. Patient table 146, which is stored in the memory of file server 112, lists the patients, their identification codes, and educational programs 148 which have been assigned to them.

Patient table 146 is generated by information entered into the assignment screen 150 of remote interface 114. Assignment screen 150, which is illustrated in FIG. 3, lists available educational programs 148, each with a corresponding check box 166, and patients, also each with a corresponding check box 168. The administrator brings up assignment screen 150 on display 116 of remote interface 114. She selects a check box 168 for a patient and then selects a check box 166 corresponding to educational program 148 to be assigned to the patient. More than one educational program 148 can be assigned to each patient. In addition, more than one patient can be assigned the same educational program 148. The administrator then selects the ASSIGN PROGRAM button 70, which stores the assignment in patient table 146. Assignment screen 150 also includes a DELETE PROGRAM button 72, which allows the administrator to erase the assignment.

New listings of patients and educational programs 148 can easily be created by the administrator by clicking on the ADD NEW PATIENT button 174 or the ADD NEW PROGRAM button 176. When these buttons are selected, a new field is added to the patient or program categories. The administrator then types in the name of the new patient or the name of the new educational program 148, and saves the addition by clicking on the SAVE NEW LISTING button 178. The new listings are then saved in patient table 146.

In the preferred embodiment, remote interface 114 is a web page. Thus, using keyboard 120, as shown in FIG. 1, the administrator can create customized educational programs 148 in the form of static or interactive web pages for patients. The administrator creates the web page using a scripting language such as HTML or Java, and then stores it on database 144. These web pages can be accessed by multimedia processor 124 in the same manner as the above mentioned educational programs 148.

Referring to FIG. 2 again, remote interface 114 also comprises a report screen 152 which is shown on display 116. Report screen 152, as illustrated in FIG. 4, tells the administrator when the patient has completed watching assigned educational program 148 and/or a program score. Specific techniques for writing report generator program to display data in this manner are well known in the art.

The program score is generally determined by evaluating the patient's responses to an interactive educational program, such as an interactive web page. FIG. 5 shows a sample educational program 148 which includes questions for the patient to answer using input device 134.

The remote education system also includes a memory card writer 18 connected to remote interface 114. Memory card writer is an apparatus which can encode information onto a magnetic strip or circuit. The process of storing information on a magnetic strip or circuit is well known. Memory card 122 produced contains the patient's identification code 156 and the file server address 154.

As shown in FIG. 2, multimedia processor 124 also comprises a memory means 160, a central computing unit (CPU) 158, a modem 164, and audiovisual display 128. Memory card reader 126, memory means 160, modem 164, and audiovisual display 128 are all connected to CPU 158. Multimedia processor 124 connects to file server 112 using modem 164 and communication link 40, which is preferably a telephone cable. Multimedia processor 124 can be programmed to automatically dial out using modem 164 whenever memory card 122 is placed in memory card reader 126.

Memory card reader 126 comprises means of detecting and interpreting the information stored on memory card 122. In the preferred embodiment, memory card reader 126 is a magnetic strip reader. When the patient places memory card 122 in memory card reader 122, the information is sent to CPU 150 and then memory means 160. The information is then sent to file server 112 by way of modem 164.

Memory means 160 of multimedia processor 124 is also for storing program instructions on how to connect to file server 112 and how to transmit patient's identification code 156. In addition, memory means 160 receives and stores assigned educational programs 148 from file server 112. When the content of educational programs 148 are sent to multimedia processor 124 from file server 112, memory means translate the content into audiovisual signals to be displayed on display 128.

Figure 6A:
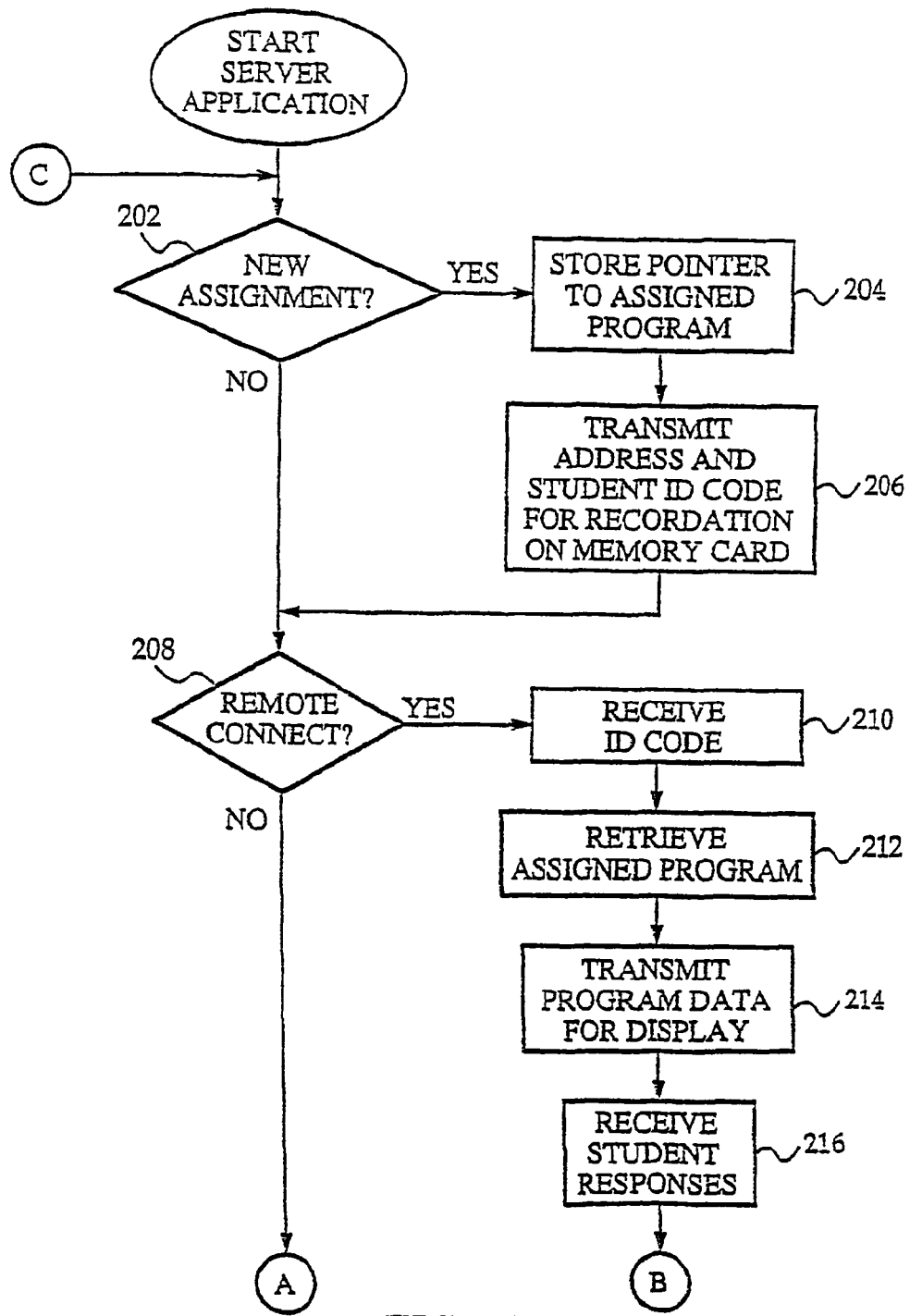
FIG. 6A is a flow chart illustrating the steps executed by the file server of the present invention as shown in FIG. 1.
Figure 6B:
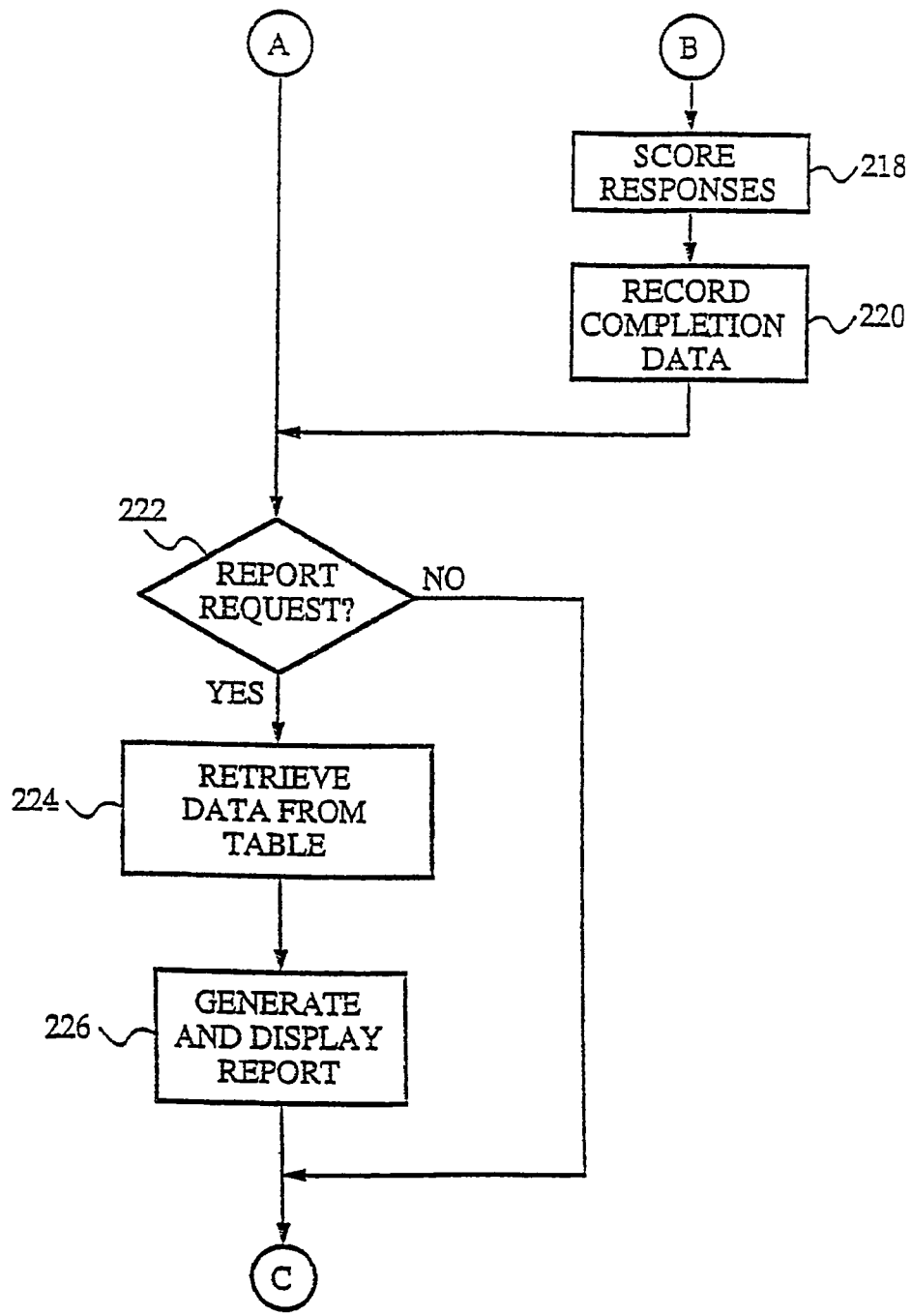
FIG. 6B is a continuation of the flow chart of FIG. 5A.

FIGS. 6A and 6B show a flowchart illustrating the steps carried out by server 112 in the preferred embodiment of the invention. In step 202, server 112 first asks if the administrator would like to create a new assignment. Creating a new assignment can mean adding a new patient to the patient list or assigning a new educational program 148 to a patient. If the administrator decides to create a new assignment, the information is stored in patent table 146, as shown in step 204. In step 206, the new assignment information consisting of the patient's identification code 156 and file server address 154 is also recorded on memory card 122 by memory card writer 118, and then given to the patient. If the administrator does not need to create a new assignment, she goes directly from step 202 to step 208.

After the patient returns home, he places memory card 122 in memory card reader 126 connected to multimedia processor 124. File server address 154 on memory card 122 allows multimedia processor 124 to locate and connect to file server 112 in step 208. Patient's identification code 156 is then sent over in step 210. In step 212, file server 112 then goes to patient table 146 and looks up educational program 148 assigned to patient. A pointer in database 144 then retrieves educational program 148. If educational program 148 is located in a remote database, it is sent through file server 112 to multimedia processor 124, as shown in step 214. Memory means 160 of multimedia processor 124 then interpret and translate the content of educational program 148 into audiovisual signals to be shown on display 128.

After the patient has watched educational program 148, completion data comprising the time and date or patient responses is sent from multimedia processor 124 to file server 112 in step 216. Step 218 scores the patient responses to determine a program score. Step 220 then records the completion data in patient table 146 of file server 112.

If the administrator wishes to view completion data of a particular patient, she can request a patient report, as shown in step 222. Step 222 can occur after the patient has watched and responded to educational program 148 in step 220, or at any time after step 208. File server 122 retrieves the patient's completion data from patient table 146, step 224, and then shows it in the form of report screen 152 on display 116 in step 226. Report screen 152 is illustrated in FIG. 4.

Figure 7:
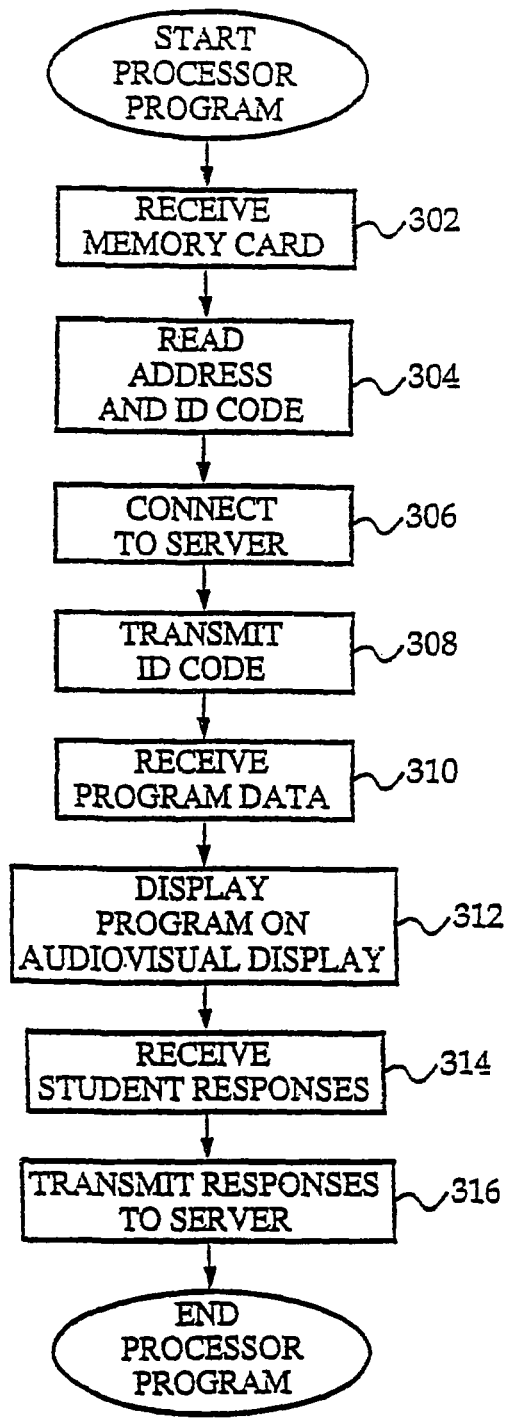
FIG. 7 is a flow chart illustrating the steps executed by the multimedia processor of the present invention as shown in FIG. 1.

FIG. 7 is a flowchart outlining the steps involved in the processor program of multimedia processor 124 in the preferred embodiment of the invention. Processor program can be carried out by known software programs. The processor program begins when memory card 122 is placed in memory card reader 126, as shown in step 302. Memory card reader 126 reads patient's identification code 304 and file server address 156 from memory card 122 in step 304, and then sends the information to CPU 158. File server address 156 allows CPU 158 to connect to server 112 via modem 164 in step 306. Patient's identification code 154 is then transmitted to file server 112 in step 308. In step 310, CPU 158 receives the content of assigned educational program 148 via modem 164. The content is converted into audiovisual signals shown on display 128 in step 312. Patient response to educational program 148 is sent to CPU 158 by input device 134. CPU 158 then sends the patient response, along with other completion data, to file server 112. The processor program of multimedia processor 124 then ends.

Memory card reader 126 of multimedia processor 124 can also have a writing function similar to that of memory card writer 118 of remote interface 114. This feature allows the patient responses to educational program to be stored on memory card 122. The patient can then bring in memory card 122 to his healthcare provider or the administrator. Memory card writer 118 of remote interface 114 must also have reading capabilities. Memory card 122 is inserted in memory card writer/reader 118 and the patient responses are downloaded into remote interface 114. This feature can be used if the patient does not wish to transmit his responses over communication link 140.

The present invention allows a healthcare provider or administrator to assign a remote educational program to a patient. The patient has the luxury of watching and responding to the program in his own home at his convenience. The patient's response to the educational program is then transmitted to the file server and displayed for the administrator to view. Thus the administrator can monitor whether or not the patient has watched the educational program, and can also evaluate his responses to the program.

Appendix A shows one implementation of the present invention as it applies to working with a diabetes patient through MEDTV™ over the Internet. MEDTV™ is a trademark of Raya Systems, Inc. (Mountain View, Calif.).

Figure 8:
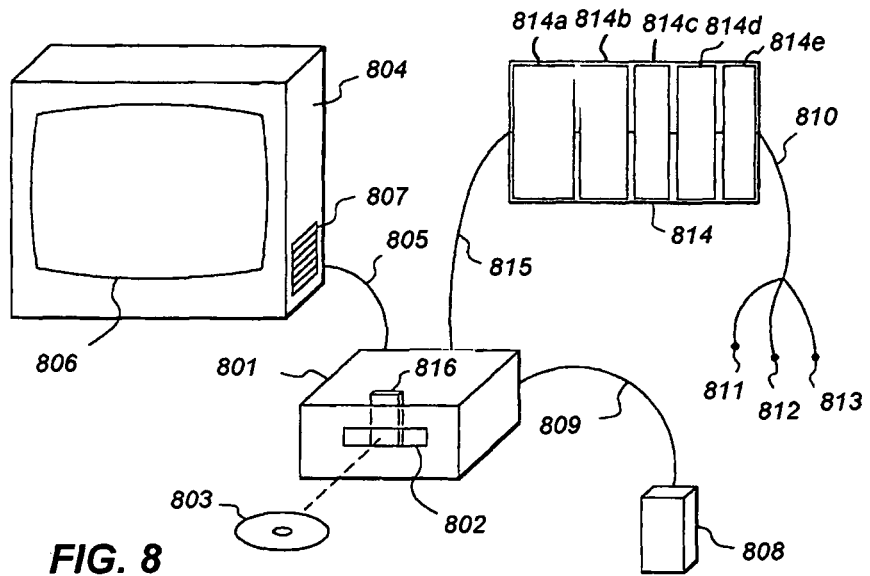
FIG. 8 shows a diagram of the present invention.
Figure 9:
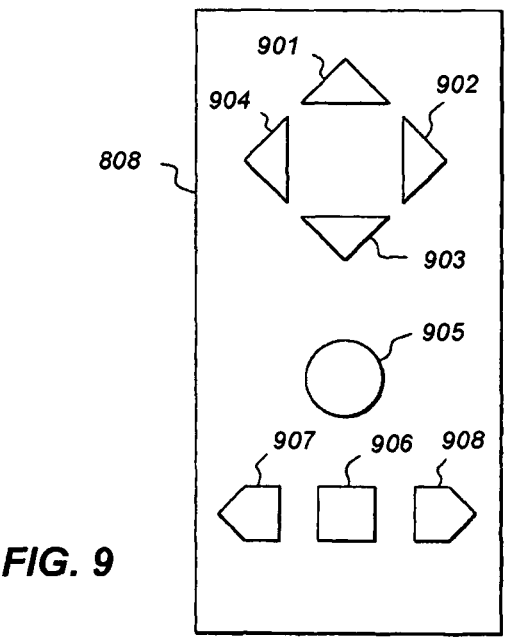
FIG. 9 shows a detailed diagram of the hand-held program controller of the present invention.

Referring to FIG. 8, a diagram of the present invention is shown. A multimedia processor 801 comprises a microprocessor, hardware, read-only digital memory (ROM), writeable digital memory (RAM), and may also include a compact disk read only memory (CD-ROM) drive for accepting interchangeable compact disks for an increased memory store. Data and software that is medically or health related and software routines for controlling the system are stored in one or more of the digital memory stores. In the preferred embodiment, the multimedia processor 801 is a CD-ROM television video game console, otherwise known as an "interactive N" (ITV) system such as the Interactive Multiplayer developed by 3DO Company and manufactured by Panasonic under the name "FZ-1 REAL 3DO Interactive Multiplayer" or another similar ITV system manufactured under license from 3DO. The multimedia processor 801 is somewhat smaller in size than a typical video cassette recorder (VCR). Alternately, the multimedia player 1 is a "set-top box" which is television compatible, has interactive capabilities and has one or more communication ports which may connect to the "information superhighway" through a telephone line, coaxial cable, or other means. Such a set-top box preferably includes an application specific integrated circuit (ASIC), programmed arithmetic logic array chip (PAL) or other circuit devices to implement functions of an interface device 814 described below. Preferably, the multimedia processor 801 also comprises a 32-bit reduced instruction set (RISC) central processing unit (CPU) made by ARM, a digital signal processor (DSP) for high quality sound, and has three dimensional audio imaging for increased directional realism in the sound effects. The multimedia processor 801 preferably has expansion ports to support additional user interface and other devices, such as keyboards, joysticks, trackballs, or modems in daisy chain fashion and to accept add-on circuits for enhanced sound, video, or processing performance. In addition, the multimedia processor 801 preferably comprises an "animation engine" having two integrated circuit chips for displaying or moving up 64 million pixels per second and having the ability to make a video image bend, twist, skew, shrink, stretch, be transparent or translucent, and having the ability to create light and shadow effects and having the ability to "wrap" a first two-dimensional video image onto a second three-dimensional video image of an object. Such video techniques are known in the art. The multimedia processor 801 has a slot 802 for accepting interchangeable compact disks 803 into the CD-ROM drive. The interchangeable compact disks 803 comprise additional software which enables the system to execute a variety of specific health related functions and interactions related to ECG, blood pressure, glucose levels, pulse rate, kidney functions and so forth. Alternatively, the interchangeable compact disks 803 are instead interchangeable cartridges, similar to interchangeable video game cartridges, having high density digital mass storage, such as flash memory cards. The multimedia processor 801 is coupled by a television interface cable 805 to a television 804 of the conventional type or to a television having enhanced video or sound capabilities. The multimedia processor 801 supplies electronic information to the television 804 through the television interface cable 805 to enable the television 804 to produce appropriate images on the television screen 806 and to enable the television 804 to project appropriate audio sounds from the television speaker 807 or speakers. Stereo sound effects may be employed in those televisions having stereo capability. In addition, auxiliary speakers or sound amplification devices may be coupled to the television 804. The multimedia processor 801 is also coupled to a program controller 808 by a control interface cable 809. The program controller 808 enables the user to make selections and to control the functions of the health monitoring system. The program controller 808 is also shown in FIG. 9 and is described in more detail below.

The multimedia processor 801 is also coupled to a physiological data monitor 810. The physiological data monitor 810 is coupled to the user's body to obtain electrical signals representative of a physiological parameter. The physiological data monitor 810 is coupled to the multimedia processor through an interface device 814. The interface device 814 includes hardware and software necessary to receive signals from the physiological data monitor 810 by means of the signal receiver 814(d), to perform signal conditioning or processing by means of the processor 814(b) and the convertor 814(c), to control the multimedia processor 801 by means of the multimedia controller 814(a), and to provide signals representative of a physiological parameter to the multimedia processor 801 through an interface cable 815. Such signal processing may include digital to analog conversion, analog to digital conversion, digital reformatting, and signal scaling and may be based upon the system hardware, software, user input or upon requirements of the physiological data monitor 810. Preferably, the physiological data monitor 810 is electrically isolated from the rest of the system by a patient isolating circuit 814(e). For example, such a patient isolating circuit may comprise an optically isolating circuit such as the "MAX250/MAX251"+5 volt powered isolated RS-232 driver/receiver manufactured by MAXIM. Preferably, the interface device 814 comprises the patient isolating circuit described above by being integrally housed within the same housing, however, the patient isolating circuit may be separately housed or incorporated into the physiological data monitor 810. In addition, the multimedia processor 801 may provide control signals to the interface device 814 through the interface cable 815 based upon the hardware and software in the multimedia processor 801 and upon the user's input to the program controller 808. Additionally, the program controller 808 may be coupled to provide control signals directly to the interface device 814. The interface device 814 may be external to the multimedia processor 801, but in the preferred embodiment, the interface device 814 and the interface cable 815 are integrally mounted internal to the housing of the multimedia processor 801 as is the patient isolating circuit.

As an example only, FIG. 8 shows a physiological data monitor 810 in the form of an electrocardiogram (ECG) monitoring device. The ECG monitoring device has three electrodes 811, 812, 813 which couple to the user's body to obtain analog electrical signals representative of the user's cardiac activity. However, the physiological data monitor 810 may comprise a pressure cuff, a temperature probe, a blood glucose sensor, kidney dialysis equipment, and so forth. Standard or modified patient monitoring equipment provided by other manufacturers may be used. For example, Johnson & Johnson makes a blood pressure cuff called "Dynamap" and Boehringer Mannheim makes a blood glucose indicator called "Accucheck Easy." Such patient monitoring equipment provided by other manufacturers often have an RS-232 port or analog output jacks. Therefore, to save manufacturing costs, the present invention includes the ability to interface with such types of connectors by including compatible connectors and related hardware in the interface device 814. Each of the various physiological data monitors 810 are interchangeable and each may have corresponding software stored on an interchangeable compact disk 803.

In an embodiment of the present invention, the multimedia processor 1 has selectable modes wherein a language such as English, French, German, Italian, or Spanish is selected and a level of sophistication or educational background of the user is selected. This may be implemented by a hardware switch coupled to the multimedia processor 801 or by a hidden software function which is accessible, for example, only when a specific combination of control buttons are activated during system power up. Such hidden software functions are known in the art. As an example of the use of the selectable modes, a doctor could select an appropriate language and level of sophistication of a user or patient using the hidden software function. The user then takes the system to the user's home and goes through an interactive health monitoring or an interactive educational program which is tailored to the language and level of sophistication or educational background of the user. The user then returns to the doctor's office with the system where information obtained from the patient is downloaded from the health monitoring system to a computer at the doctor's office. This information then enables the doctor to quickly pinpoint any problem areas that the particular patient is experiencing which saves the doctor's time, effecting a savings in medical resources. Then the system may be reconfigured for a different user having a different native language and level of sophistication or educational background and the process repeated.

Referring to FIG. 9, a hand-held program controller 808 is shown. The program controller 808 comprises a variety of push button switches. The push button switches are coupled to be activated by control buttons 901, 902, 903, 904, 905, 906, 907, and 908 which are manipulated by the user for controlling the health monitoring system. The program controller 808 has a group of directional control buttons 901, 902, 903 and 904 in the center of which is printed the label "SELECT." The button 905 is printed with the label "INDEX." Another button (not shown) is printed with the label "HELP." The button 906 is printed with the label "GO." Another button (not shown) is printed with the label "PAUSE." The button 907 has the label "BACK" printed on or near it. The button 908 has the label "FORWARD" printed on or near it. The specific configuration of the buttons and labels is by way of example only and it should be apparent that any number of alternate configurations of buttons, keys, or different labels would suffice to achieve the objects of the program controller 808.

As an example of how the health monitoring system operates, a user first sets up the system in a manner similar to setting up a television-type video game, such as that manufactured by 3DO. Next, an interchangeable compact disk 803 is inserted into the slot 802 of the multimedia processor 801. In this case, an ECG disk is installed. Then, the user connects the physiological data monitor 810 to the user's body. In this case, the ECG electrodes 811, 812, 813 are attached to the user's chest. Next, the user turns the system on. Then the software of the interchangeable compact disk 803 and the software of the multimedia processor 801 guide the user through a series of educational and interactive steps including measurements of physiological parameters and display of the results. In this case, for example, the health monitoring system may display on the television screen a moving or still image or images and possibly audio signals to explain what an ECG is, why ECG measurements are important to health care and to guide the user through the steps necessary to take ECG measurements. Then, the health monitoring system displays the results of the measurements and may have audio effects as well. In this case, the user's ECG trace or waveform may be displayed in analog form along with the user's heart rate in numerical form, while a audio representation of the user's beating heart may be present. The health monitoring system may also compare the user's measurements with previously stored measurements of the same user's ECG or with measurements representative of a normative physiological parameter. Based upon these comparisons, the system may guide the user through additional measurements, store information for later retrieval or downloading, recommend that the user seek the services of a health care professional, ask questions of the user, give advice in areas such as the user's diet and exercise habits, and so forth. In addition to the above, the health monitoring system may provide functions related to blood pressure, glucose levels, pulse rate, kidney function, and so forth.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention. Specifically, it will be apparent that to one of ordinary skill in the art that the device of the present invention could be implemented in several different ways and the apparatus disclosed above is only illustrative of the preferred embodiment of the invention and is in no way a limitation.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible, as this invention can be used in any field where it is desirable to remotely educate an individual. For example, teachers can use it to assign lessons to their students, and employers can use it to provide additional job training for their employees.

Another embodiment of the present invention allows companies to promote their products. Preprogrammed memory cards can be placed with a company's products. When the consumer buys a product, he also receives the preprogrammed memory card, which contains the product identification code and the address of the company's consumer-product file server. When the consumer places the memory card in the memory card reader of his multimedia processor, the multimedia processor automatically connects to the company's file server. The file server contains a consumer-product table which stores a list of all the company's products with corresponding pointers to relevant educational programs or advertisements. For example, a sunblock product would have a pointer to a short video on basic sun safety, as well as an advertisement for all sunblock products made by that company.

When the file server receives the product identification code from the multimedia processor, it retrieves the relevant educational program or advertisement and sends it back to the consumer's multimedia processor. The consumer can then watch the program or advertisement on the display.

Considering all the possibilities of the remote education system, the scope of the invention should be determined not by the examples given, but by the appended claims and their legal equivalents.

The embodiments of the invention in which an exclusive property or privilege is claimed are defined as follows:

1. A blood glucose monitoring system for monitoring a blood glucose level and for providing health-related information comprising:
   (a) a display device including a display screen which displays the blood glucose level as measured;
   (b) an audio speaker;
   (c) a processor configured to provide audio and visual signals to the audio speaker and the display device respectively;
   (d) at least one built-in memory including read-only digital memory (ROM) or writeable digital memory (RAM), or both, having stored therein operation data and operation software routines executable by the processor for:
      (i) controlling the blood glucose monitoring system;
      (ii) comparing the blood glucose level as measured with stored measurements;
      (iii) performing one or more further processing functions in response to the comparing;
      (iv) connecting the processor to a remotely located computer via a communication network in response to receiving a network address of the remotely located computer from a removable memory card attached to the system, wherein (a) the network address identifies the remotely located computer within the communication network and (b) the remotely located computer is located distant from the processor; and
      (v) receiving the health-related information at the processor via the communication network from the remotely located computer;
   (e) at least one physiological data monitor configured to (i) provide a measurement signal representative of a physiological parameter of a user and (ii) reside outside a first housing containing said processor; and
   (f) an input device in communication with the processor and configured to (i) receive an input from the user including an identification code, (ii) enable the user to (1) make selections and (2) control one or more user functions of the blood glucose monitoring system and (iii) provide a control signal to the processor based upon the input, thereby to cause the health related information to be provided to the user based upon (a) the measurement signal representative of the blood glucose level, (b) the identification code received from said user, and (c) a destination address programmed by a physician prior to the user receiving the processor, wherein the physiological parameter includes the blood glucose level and the physiological data monitor includes a blood glucose indicator.

2. The system according to claim 1 wherein the input device is hand-held.

3. The system according to claim 1, wherein the input device receives the input from the user through at least one push button switch.

4. The system according to claim 1, wherein the health related information provided from the remotely located computer to the user includes moving images displayed on the display screen.

5. The system according to claim 4, wherein the health related information provided from the remotely located computer to the user further includes a comparison of measurements of the blood glucose level with previously stored measurements of the blood glucose level.

6. The system according to claim 4, wherein the health related information provided from the remotely located computer to the user includes educational information.

7. The system according to claim 1, wherein the blood glucose monitoring system is configured to store particular information on the at least one built-in memory for later retrieval.

8. The system according to claim 1, wherein the display device is a television.

9. The system according to claim 1, further comprising one or more communication ports configured to connect the blood glucose monitoring system to an information superhighway.

10. The system according to claim 1, further comprising a slot for accepting a flash memory card.

11. The system according to claim 1, wherein the blood glucose monitoring system is configured for downloading particular information obtained from the user to a separate computer.

12. The system according to claim 1, wherein the at least one built-in memory further has stored therein alarm data and alarm software routines for triggering an alarm if the blood glucose level as measured falls outside a predetermined range.

13. The system according to claim 1, wherein the operational data and the operation software routines are configured to guide the user through additional measurements based on the comparing.

14. The system according to claim 1, wherein the operational data and the operation software routines are configured to store particular information to support later retrieval or downloading based on the comparing.

15. The system according to claim 1, wherein the operational data and the operation software routines are configured to recommend a certain action be taken by the user based on the comparing.

16. The system according to claim 1, wherein the operational data and the operation software routines are configured to ask questions of the user based on the comparing.

17. The system according to claim 1, wherein the operational data and the operation software routines are configured to give advice as to diet or exercise habits of the user based on the comparing.

18. The system, according to claim 1, wherein the input device is in wireless communications with the processor.

19. The system according to claim 1, wherein the physiological data monitor and the input device are in a second housing separate from the first housing containing the processor.

20. A system for interactively monitoring a blood glucose level and for interactively providing health-related information comprising:
(a) a glucose monitor adapted to measure the blood glucose level of a user and for generating a first signal in response to a measurement of the blood glucose level;
(b) a processor (i) for receiving a second signal that is a function of the first signal and (ii) being contained within a housing, said glucose monitor being disposed outside said housing containing said processor;
(c) a memory coupled to the processor for storing blood glucose level data, the memory including read-only digital memory (ROM) or writeable digital memory (RAM), or both, having stored therein operation data and operation software routines executable by the processor for:
(i) controlling the system;
(ii) comparing the blood glucose level as measured with stored measurements;
(iii) performing one or more further processing functions in response to the comparing;
(iv) connecting the processor to a remotely located computer via a communication network in response to receiving a network address of the remotely located computer from a removable memory card attached to the system, wherein (a) the network address identifies the remotely located computer within the communication network and (b) the remotely located computer is located distance from the processor; and
(v) receiving the health-related information at the processor via the communication network from the remotely located computer;
(d) a display system coupled to the processor for displaying a representation of the blood glucose level, so as to provide the health related information to the user in an interactive manner based upon (a) the first signal representative of the blood glucose level, (b) an identification code received from said user, and (c) a destination address programmed by a physician prior to the user receiving the processor; and
(e) an input device (i) in communication with the processor, (ii) enabling the user (1) to make selections and (2) to control one or more user functions of the system and (iii) provide a control signal to the processor based upon the input.

21. The system according to claim 20, further comprising one or more communication ports configured to connect the system to an information superhighway.

22. The system according to claim 20, further comprising a slot for accepting a flash memory card.

23. The system according to claim 20, wherein the system is configured for downloading particular information obtained from the user to a separate computer.

24. The system according to claim 20, wherein the memory further has stored therein alarm data and alarm software routines for triggering an alarm if the blood glucose level as measured falls outside a predetermined range.

25. A method for monitoring a physiological condition and for providing health-related information with a system, the method comprising:
(a) using at least one physiological data monitor to provide a measurement signal representative of a user physiological parameter;
(b) providing a processor to produce audio and visual signals for reproduction at an audio speaker and a display screen, respectively, and (i) providing said processor within a housing and (ii) said physiological data monitor being disposed outside said housing containing said processor;
(c) using an input device in communication with the processor to (i) receive an input from the user and (ii) provide one or more controller signals to the processor based upon the input from the user;
(d) in response to and based upon (i) the measurement signal representative of the user physiological parameter and (ii) the input from the user, having the processor cause the visual and the audio signals of the health related information to be presented to the user, wherein the user physiological parameter includes a blood glucose level and the physiological data monitor includes a blood glucose indicator;
(e) providing a memory coupled to the processor, the memory including read-only digital memory (ROM) or writeable digital memory (RAM), or both, the memory having stored therein the blood glucose level and operation software routines executable by the processor for:
(i) controlling the system;
(ii) comparing the blood glucose level as measured with stored measurements;
(iii) performing one or more further processing functions in response to the comparing;
(iv) connecting the processor to a remotely located computer via a communication network in response to receiving a network address of the remotely located computer from a removable memory card attached to the system, wherein (a) the network address identifies the remotely located computer within the communication network and (b) the remotely located computer is located distant from the processor; and
(v) receiving the health-related information at the processor via the communication network from the remotely located computer based upon (a) the measurement signal representative of the blood glucose level, (b) an identification code received from said user, and (c) a destination address programmed by a physician prior to the user receiving the processor.

26. The method according to claim 25 wherein the input device is hand-held.

27. The method according to claim 25, wherein the input device receives the input from the user through at least one push button switch.

28. The method according to claim 25, wherein the health related information provided from the remotely located computer to the user includes moving images displayed on the display screen.

29. The method according to claim 28, wherein the health related information provided from the remotely located computer to the user further includes a comparison of measurements of the user physiological parameter with previously stored measurements of the user physiological parameter.

30. The method according to claim 28, wherein the health related information provided from the remotely located computer to the user includes educational information.

31. The method according to claim 25, further comprising storing particular information in the memory for later retrieval.

32. The method according to claim 25, wherein the display screen comprises a television, and the visual signals are reproduced on the television.

33. The method according to claim 25, further comprising connecting to an information superhighway.

34. The method according to claim 25, further comprising accepting a flash memory card into a pre-configuration slot.

35. The method according to claim 25, further comprising downloading particular information obtained from the user to a separate server.

36. The method according to claim 25, wherein the memory further has stored therein alarm data and alarm software routines for triggering an alarm if the blood glucose level as measured falls outside a predetermined range.

37. An apparatus for interactively monitoring a blood glucose level and for interactively providing health-related information comprising:
   a. a display device comprising a display screen;
   b. a processor coupled to provide a visual signal to the display screen, wherein the processor is contained within a housing;
   c. a glucose monitor coupled to provide a measurement signal representative of the blood glucose level to the processor;
   d. at least one built-in memory, including read-only digital memory (ROM) or writeable digital memory (RAM), or both, having stored therein operation data and operation software routines executable by the processor for:
      (i) controlling the apparatus;
      (ii) comparing the blood glucose level as measured with stored measurements;
      (iii) performing one or more further processing functions in response to the comparing;
      (iv) connecting the processor to a remotely located computer via a communication network in response to receiving a network address of the remotely located computer from a removable memory card attached to the apparatus, wherein (a) the network address identifies the remotely located computer within the communication network and (b) the remotely located computer is located distant from the processor; and
      (v) receiving the health-related information at the processor via the communication network from the remotely located computer; and
   e. an input device in communication with the processor and configured to (i) receive an input from the user, (ii) enable the user (1) to make selections and (2) to control one or more user functions of the apparatus; and (iii) provide a control signal to the processor based upon the input from the user, wherein health related information is sent to said user based upon (a) the measurement signal representative of the blood glucose level, (b) an identification code received from said user, and (c) a destination address programmed by a physician prior to the user receiving the processor.

38. The apparatus according to claim 37 wherein the processor comprises a video game console.

39. The apparatus according to claim 37 wherein the display device comprises a television set.

40. The apparatus according to claim 37, further comprising:
   a CD-ROM drive; and
   an interchangeable compact disk removably coupled to the CD-ROM drive for providing additional functionality to the processor.

41. The apparatus according to claim 37, further comprising one or more communication ports configured to connect the system to an information superhighway.

42. The apparatus according to claim 37, further comprising a slot for accepting a flash memory card.

43. The apparatus according to claim 37, wherein the apparatus is configured for downloading particular information obtained from the user to a separate computer.

44. The apparatus according to claim 37, wherein the memory further has stored therein alarm data and alarm software routines for triggering an alarm if the blood glucose level as measured falls outside a predetermined range.

45. An apparatus for interactively monitoring a blood glucose level and for interactively providing health-related information comprising:
   a. a display device comprising a display screen and an audio speaker;
   b. a processor contained within a housing and coupled to provide a visual signal to the display screen;
   c. a glucose monitor coupled to provide a measurement signal representative of the blood glucose level of a user to the processor;
   d. at least one built-in memory, including read-only digital memory (ROM) or writeable digital memory (RAM), or both, having stored therein operation data and operation software routines executable by the processor for:
      (i) controlling the apparatus;
      (ii) comparing the blood glucose level as measured with stored measurements;
      (iii) performing one or more further processing functions in response to the comparing;
      (iv) connecting the processor to a remotely located computer via a communication network in response to receiving a network address of the remotely located computer from a removable memory card attached to the apparatus, wherein (a) the network address identifies the remotely located computer within the communication network and (b) the remotely located computer is located distant from the processor; and
      (v) receiving the health-related information at the processor via the communication network from the remotely located computer; and
   e. an input device in communication with the processor and configured to (i) receive an input from the user, (ii) enable the user to (1) make selections and (2) control one or more user functions of the apparatus and (iii) provide a control signal to the processor based upon the input, wherein health related information is sent to said user based upon (a) the measurement signal representative of the blood glucose level, (b) an identification code received from said user, and (c) a destination address programmed by a physician prior to the user receiving the processor.

46. The apparatus according to claim 45 wherein the processor comprises a video game console.

47. The apparatus according to claim 45 further comprising:
a CD-ROM drive; and
an interchangeable compact disk removably coupled to the CD-ROM drive for providing additional functionality to the processor.

48. The apparatus according to claim 45, further comprising one or more communication ports configured to connect the system to an information superhighway.

49. The apparatus of claim 45, further comprising a slot for accepting a flash memory card.

50. The apparatus according to claim 45, wherein the apparatus is configured for downloading particular information obtained from the user to a separate computer.

51. The apparatus according to claim 45, wherein the memory further has stored therein alarm data and alarm software routines for triggering an alarm if the blood glucose level as measured falls outside a predetermined range.

\* \* \* \* \*